United States Patent
Kuduk et al.

(10) Patent No.: US 7,163,951 B2
(45) Date of Patent: Jan. 16, 2007

(54) N-BIARYLMETHYL AMINOCYCLOALKANECARBOXAMIDE DERIVATIVES

(75) Inventors: Scott D. Kuduk, Harleysville, PA (US); Michael R. Wood, Harleysville, PA (US); Mark G. Bock, Hatfield, PA (US)

(73) Assignee: Merck & Co., Inc., Rahway, NJ (US)

( * ) Notice: Subject to any disclaimer, the term of this patent is extended or adjusted under 35 U.S.C. 154(b) by 66 days.

(21) Appl. No.: 10/523,911

(22) PCT Filed: Aug. 25, 2003

(86) PCT No.: PCT/US03/26628

§ 371 (c)(1), (2), (4) Date: Feb. 8, 2005

(87) PCT Pub. No.: WO2004/019868

PCT Pub. Date: Mar. 11, 2004

(65) Prior Publication Data

US 2005/0288305 A1    Dec. 29, 2005

Related U.S. Application Data

(60) Provisional application No. 60/406,742, filed on Aug. 29, 2002.

(51) Int. Cl.
*A61K 31/4427* (2006.01)
*C07D 401/12* (2006.01)

(52) U.S. Cl. .............. 514/336; 546/268.1; 546/268.7; 546/337; 544/296; 544/333; 514/256; 514/269; 514/340; 514/342; 514/357

(58) Field of Classification Search ............ 514/336, 514/269, 340, 342, 357; 546/268.1, 268.7, 546/337; 544/296, 333
See application file for complete search history.

(56) References Cited

U.S. PATENT DOCUMENTS

| 5,023,265 A | 6/1991 | Scherlock et al. |
| 6,919,343 B1 | 7/2005 | Wood et al. |
| 2005/0085667 A1 | 4/2005 | Wood et al. |

FOREIGN PATENT DOCUMENTS

CA    2050769    3/1992

*Primary Examiner*—Charanjit S. Aulakh
(74) *Attorney, Agent, or Firm*—David L. Rose; Mollie M. Yang

(57) ABSTRACT

N-Biarylmethylaminocycloalkanecarboxamide derivatives are bradykinin B1 antagonists or inverse agonists useful in the treatment or prevention of symptoms such as pain and inflammation associated with the bradykinin B1 pathway.

26 Claims, No Drawings

N-BIARYLMETHYL AMINOCYCLOALKANECARBOXAMIDE DERIVATIVES

CROSS REFERENCE TO RELATED APPLICATIONS

This application is the National Stage of International Application No. PCT/US03/26628, filed Aug. 25, 2003 which claims the benefit under 35 U.S.C. 119(e) of U.S. Provisional Application No. 60/406742, filed August 29, 2002.

BACKGROUND OF THE INVENTION

This invention is directed to aminocycloalkanecarboxamide compounds. In particular, this invention is directed to aminocycloalkanecarboxamide compounds that are bradykinin antagonists or inverse agonists.

Bradykinin ("BK") is a kinin which plays an important role in the pathophysiological processes accompanying acute and chronic pain and inflammation. Bradykinin (BK), like other kinins, is an autacoid peptide produced by the catalytic action of kallikrein enzymes on plasma and tissue precursors termed kininogens. The biological actions of BK are mediated by at least two major G-protein-coupled BK receptors termed B1 and B2. It is generally believed that B2 receptors, but not B1 receptors, are expressed in normal tissues and that inflammation, tissue damage or bacterial infection can rapidly induce B1 receptor expression. This makes the B1 receptor a particularly attractive drug target. The putative role of kinins, and specifically BK, in the management of pain and inflammation has provided the impetus for developing potent and selective BK antagonists. In recent years, this effort has been heightened with the expectation that useful therapeutic agents with analgesic and anti-inflammatory properties would provide relief from maladies mediated through a BK receptor pathway (see e.g., M. G. Bock and J. Longmore, Current Opinion in Chem. Biol., 4:401–406(2000)). Accordingly, there is a need for novel compounds that are effective in blocking or reversing activation of bradykinin receptors. Such compounds would be useful in the management of pain and inflammation, as well as in the treatment or prevention of diseases and disorders mediated by bradykinin; further, such compounds are also useful as research tools (in vivo and in vitro).

Canadian Published Application No. 2,050,769 discloses compounds of the formula:

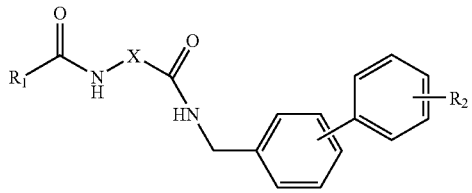

which are intermediates in the preparation of angiotensin II antagonists.

SUMMARY OF THE INVENTION

The present invention provides biaryl cycloalkanecarboxamide derivatives which are bradykinin antagonists or inverse agonists, pharmaceutical compositions containing such compounds, and methods of using them as therapeutic agents.

DETAILED DESCRIPTION OF THE INVENTION

The present invention provides compounds of formula I and pharmaceutically acceptable salts thereof:

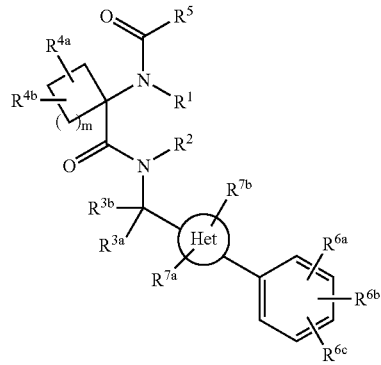

I wherein
Het is pyrimidinyl or pyridyl, or N-oxide thereof
$R^1$ and $R^2$ are independently selected from hydrogen and $C_{1-4}$ alkyl
$R^{3a}$ and $R^{3b}$ are independently selected from hydrogen and $C_{1-4}$ alkyl optionally substituted with 1 to 5 halogen atoms
$R^{4a}$ and $R^{4b}$ are independently selected from hydrogen, halogen, and $C_{1-4}$ alkyl optionally substituted with 1 to 4 groups selected from halogen, $OR^a$, $OC(O)R^a$, $S(O)_k R^d$, $OS(O)_2 R^d$, and $NR^1 R^2$, or
$R^{4a}$ and $R^{4b}$ together with the carbon atom to which they are both attached form an exo-cyclic methylene optionally substituted with 1 to 2 groups selected from $C_{1-4}$ alkyl optionally substituted with 1–5 halogen atoms and $C_{1-4}$ alkyloxy
$R^5$ is selected from (1) $C_{1-6}$ alkyl optionally substituted with 1 to 5 groups independently selected from halogen, nitro, cyano, $OR^a$, $SR^a$, $COR^a$, $SO_2 R^d$, $CO_2 R^a$, $OC(O)R^a$, $NR^b R^c$, $NR^b C(O)R^a$, $NR^b C(O)_2 R^a$, $C(O)NR^b R^c$, $C_{3-8}$ cycloalkyl, (2) $C_{3-8}$ cycloalkyl optionally substituted with 1 to 5 groups independently selected from halogen, nitro, cyano and phenyl, (3) $C_{3-6}$ alkynyl, (4) $C_{2-6}$ alkenyl optionally substituted with hydroxyethyl, (5) $(CH_2)_k$-aryl optionally substituted with 1 to 3 groups independently selected from halogen, nitro, cyano, $OR^a$, $SR^a$, $C(O)_2 R^a$, $C_{1-4}$ alkyl and $C_{1-3}$ haloalkyl, wherein aryl is selected from phenyl, 3,4-methylenedioxyphenyl and naphthyl, (6) $(CH_2)_k$-heterocycle optionally substituted with 1 to 3 groups independently selected from halogen, nitro, cyano, $OR^a$, $SR^a$, $C_{1-4}$ alkyl and $C_{1-3}$ halo-alkyl wherein said heterocycle is selected from (a) a 5-membered heteroaromatic ring having a ring heteroatom selected from N, O and S, and optionally having up to 3 additional ring nitrogen atoms wherein said ring is optionally benzo-fused; (b) a 6-membered heteroaromatic ring containing from 1 to 3 ring nitrogen atoms and N-oxides thereof, wherein said ring is optionally benzo-fused; and (c) a 5- or 6-membered non-aromatic heterocyclic ring selected from tetrahydrofuranyl, 5-oxotetrahydrofuranyl, 2-oxo-2H-pyranyl, and 6-oxo-1,6-dihydropyridazinyl, (7) $C(O)_2 R^a$, (8) $C(O)NR^b R^c$, and (9) $NR^b CO_2 R^a$;
$R^{6a}$ is selected from (1) $C_{1-8}$ alkyl optionally substituted with 1–5 groups independently selected from halogen, nitro, cyano, $COR^a$, $CO_2 R^a$, $C(O)NR^b R^c$, $OR^a$, $OC(O)R^a$, $SR^a$, $SO_2 R^d$, $S(O)R^d$, $NR^b R^c$, $NR^b C(O)R^a$, $NR^b SO_2 R^d$, and $NR^b CO_2 R^a$, (2) $C_{3-8}$ cycloalkyl, (3) $C_{2-8}$ alkenyl optionally substituted with CO₂Rᵃ, (4) halogen, (5) cyano, (6) nitro, (7) NRᵇRᶜ, (8) NRᵇC(O)Rᵃ, (9) NRᵇCO₂Rᵃ, (10) NRᵇC(O)NRᵇRᶜ, (11) NRᵇC(O)NRᵇCO₂Rᵃ, (12) NRᵇSO₂Rᵈ, (13) CO₂Rᵃ, (14) CORᵃ, (15) C(O)NRᵇRᶜ, (16) C(O)NHORᵃ, (17) C(=NORᵃ)Rᵃ, (18) C(=NORᵃ)NRᵇRᶜ, (19) ORᵃ, (20) OC(O)ₖRᵃ, (21) S(O)ₖRᵈ, (22) SO₂NRᵇRᶜ, and (23) optionally substituted heterocycle where the heterocycle is selected from (a) a 5-membered heteroaromatic ring having a ring heteroatom selected from N, O and S, and optionally having up to 3 additional ring nitrogen atoms, (b) 4,5-dihydrooxazolyl, and (3) 4,5-dihydro-1,2,4-oxadiazolyl, and wherein said substituent is 1 to 3 groups independently selected from C₁₋₄ alkyl optionally substituted with 1 to 5 halogen atoms, ORᵃ or OC(O)Rᵃ, R⁶ᵇ and R⁶ᶜ are independently selected from hydrogen, and a group from R⁶ᵃ; with the proviso that not more than one of R⁶ᵃ, R⁶ᵇ, and R⁶ᶜ is a heterocycle R⁷ᵃ and R⁷ᵇ are independently selected from hydrogen, halogen, cyano, nitro, ORᵃ, CO₂Rᵃ, C(O)NRᵇRᶜ, NRᵇRᶜ, and SO₂Rᵈ

Rᵃ is selected from (1) hydrogen, (2) C₁₋₄ alkyl optionally substituted with 1 to 5 halogen atoms, (3) phenyl optionally substituted with 1 to 3 groups independently selected from halogen, cyano, nitro, OH, C₁₋₄ alkyloxy, C₃₋₆ cycloalkyl and C₁₋₄ alkyl optionally substituted with 1 to 5 halogen atoms, (4) C₃₋₆ cycloalkyl, and (5) pyridyl Rᵇ and Rᶜ are independently selected from (1) hydrogen, (2) C₁₋₄ alkyl optionally substituted with 1 to 5 groups independently selected from halogen, amino, mono-C₁₋₄ alkylamino, di-C₁₋₄alkylamino, and SO₂Rᵈ, (3) (CH₂)ₖ-phenyl optionally substituted with 1 to 3 groups selected from halogen, cyano, nitro, OH, C₁₋₄ alkyloxy, C₃₋₆ cycloalkyl and C₁₋₄ alkyl optionally substituted with 1 to 5 halogen atoms, and (4) C₃₋₆ cycloalkyl, or Rᵇ and Rᶜ together with the nitrogen atom to which they are attached form a 4-, 5-, or 6-membered ring optionally containing an additional heteroatom selected from N, O, and S; or Rᵇ and Rᶜ together with the nitrogen atom to which they are attached form a cyclic imide;

Rᵈ is selected from (1) C₁₋₄ alkyl optionally substituted with 1 to 5 halogen atoms, (2) C₁₋₄ alkyloxy, and (3) phenyl optionally substituted with 1 to 3 groups selected from halogen, cyano, nitro, OH, C₁₋₄ alkyloxy, C₃₋₆ cycloalkyl and C₁₋₄ alkyl optionally substituted with 1 to 5 halogen atoms;

k is 0, 1 or 2; and m is 0, 1, 2 or 3.

In formula I, "Het" includes 2,3-pyridinediyl, 2,4-pyridinediyl, 2,5-pyridinediyl, 2,6-pyridinediyl, 3,4-pyridinediyl, 3,5-pyridinediyl, 2,4-pyrimidinediyl and 2,5-pyrimidinediyl. In one embodiment, the "Het" group is 2,5-pyridinediyl (a); in another embodimentm, the "Het" group is 2,5-pyrimidinediyl (b).

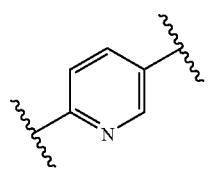

(a)

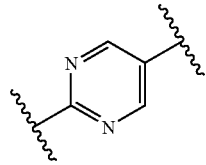

(b)

For compounds of formula I, examples of R¹ and R² include hydrogen, methyl, ethyl, n-propyl, isopropyl, n-butyl, t-butyl, isobutyl and sec-butyl. In one embodiment of formula I are compounds wherein R¹ and R² are each hydrogen.

Examples of R³ᵃ and R³ᵇ for compounds of formula I include hydrogen, methyl, ethyl, n-propyl, isopropyl, n-butyl, t-butyl, isobutyl, sec-butyl, chloromethyl, fluromethyl, trifluoromethyl, 2,2,2-trifluoroethyl, 2,2-difluoroethyl, 1,1,2,2,2-pentafluoroethyl, and the like. In one embodiment of formula I are compounds wherein one of R³ᵃ and R³ᵇ is hydrogen and the other is hydrogen or C₁₋₄ alkyl. In one subset R³ᵃ and R³ᵇ are each hydrogen, and in another subset one of R³ᵃ and R³ᵇ is hydrogen and the other methyl.

Examples R⁴ᵃ and R⁴ᵇ for compounds of formula I include hydrogen, methyl, ethyl, n-propyl, isopropyl, n-butyl, sec-butyl, isobutyl, t-butyl, chlorine, fluorine, bromine, chloromethyl, 1-chloroethyl, hydroxymethyl, 2-methoxyethyl, ethoxymethyl, acetyloxymethyl, methylthiomethyl, aminomethyl, methylaminomethyl, (dimethylamino)methyl, (methylsulfonyl)oxymethyl, and the like; or R⁴ᵃ and R⁴ᵇ on the same carbon atom taken together represent methylene. In one embodiment of formula I are compounds wherein one of R⁴ᵃ and R⁴ᵇ is hydrogen and the other is selected from hydrogen, halogen and C₁₋₄ alkyl optionally substituted with a group selected from halogen, ORᵃ, OC(O)Rᵃ, S(O)ₖRᵈ, OS(O)₂Rᵈ, and NR¹R², or R⁴ᵃ and R⁴ᵇ together with the carbon atom to which they are both attached form an exo-cyclic methylene. In one subset R⁴ᵃ and R⁴ᵇ are each hydrogen; in another subset R⁴ᵃ is hydrogen and R⁴ᵇ is selected from CH₂-halogen, CH₂—ORᵃ, CH₂—OC(O)Rᵃ, CH₂—S(O)ₖRᵈ, CH₂—OS(O)₂Rᵈ, and CH₂—NR¹R²; in a further subset R⁴ᵃ is hydrogen and R⁴ᵇ is selected from hydroxymethyl, acetyloxymethyl, chloromethyl, (methanesulfonyl)oxymethyl, (methylthio)-methyl and (dimethylamino)methyl.

Examples of R⁵ for compounds of formula I include methyl, ethyl, n-propyl, isopropyl, n-butyl, sec-butyl, isobutyl, t-butyl, 1-ethylpropyl, 2,2-dimethylpropyl, bromomethyl, chloromethyl, dichloromethyl, difluoromethyl, trifluoromethyl, chlorodifluoromethyl, cyano-methyl, aminomethyl, acetylaminomethyl, dimethylaminomethyl, hydroxymethyl, methoxy-methyl, ethoxymethyl, methylsulfonylmethyl, phenylthiomethyl, phenoxymethyl, 1-aminoethyl, 1-acetylaminomethyl, 1-imidazolylmethyl, t-butoxycarbonylaminomethyl, 3-pyridylcarbonyl-methyl, 1-chloroethyl, 1,1-dichloroethyl, 2,2,2-trifluoroethyl, pentafluoroethyl, 2-methoxyethyl, 2-phenylethyl, 2-cyclopentylethyl, 2-carboxyethyl, 2-methoxy-2-oxoethyl, 2-nitroethyl, 1,1-difluoro-1-hydroxypropyl, 1-hydroxypropyl, 2-oxopropyl, 3-methoxy-3-oxopropyl, 1-cyano-cyclopropyl, cyclopropyl, 2,2-difluorocyclopropyl, cyclopentyl, 2-phenylcyclopropyl, allyl, ethenyl, 1-(1-hydroxyethyl)vinyl, 3-butynyl, propargyl, phenyl, benzyl, 3,5-bis(trifluoromethyl)-phenyl, 2,4-difluorophenyl, 4-methylphenyl, 3,4-dimethoxybenzyl, 3,4-dimethoxyphenyl, 4-cyanophenyl, 3-nitrophenyl, 2-naphtyl, 3,4-methylenedioxyphenyl, 3-cyanophenyl, 2-cyano-phenyl, 3-fluorophenyl, 3-methoxyphenyl, 3-chlorophenyl, 3,4-dichlorophenyl, 3,5-dimethoxyphenyl, 3-trifluoromethylphenyl, 3-methylphenyl, 3,5-dichlorophenyl, 2-hydroxyphenyl, 3-hydroxyphenyl, 3-nitro-5-(trifluoromethyl)phenyl, 5-isoxazolyl, 5-isothiazolyl, 1,2,5-thiadiazolyl, 2-benzothienyl, 2-thienylmethyl, 3-pyridyl, 4-pyridyl, 2-furyl, 3-furyl, 2-thienyl, 3-thienyl, 5-methyl-3-isoxazolyl, 3-tetrahydrofuranyl, 4-methyl-1,2,5-oxadiazol-3-yl, 5-carboxy-3-pyridyl, 6-hydroxy-2-pyridyl, 5-hydroxy-3-pyridyl, 2-hydroxy-3-pyridyl, 2-methyoxy-3-pyridyl, 6-chloro-2-pyridyl, 2-chloro-3-pyridyl, 5-chloro-3-pyridyl, 5-fluoro-3-pyridyl, 5-bromo-3-pyridyl, 5-methyl-3-pyridyl, 3-(trifluoromethyl)4-pyridyl, 5-(trifluoromethyl)-3-pyridyil, 1-methyl-4-pyrazolyl, 1-pyrazolylmethyl, 1-methyl-2-imidazolyl, 1,2,4-triazol-1-ylmethyl, 4-thiazolyl, 5-oxo-tetrahydrofuran-2-yl, 2-oxo-5-pyranyl, 3-isoxazolyl, 3-pyridazinyl, 5-pyrimidinyl, 4-pyrimidinyl, 1-methyl-5-pyrazolyl, 1-methyl-3-pyrazolyl, 5-thiazolyl, 5-methyl-1-pyrazolylmethyl, (3-methyl-1,2,4-triazol-5-yl)methyl, 2-(1,2,4triazol-1-yl)ethyl, 5-methyl-4-thiazolyl, 2quinoxalinyl, methoxycarbonyl, aminocarbonyl, methylaminocarbonyl, dimethyl-aminocarbonyl, 2-(dimethylamino)ethylaminocarbonyl, benzylaminocarbonyl, 2-phenethyl-aminocarbonyl.

In one embodiment of formula I are compounds wherein $R^5$ is $C_{1-6}$ alkyl optionally substituted with 1 to 5 groups independently selected from halogen, nitro, cyano, $OR^a$, $SR^a$, $COR^a$, $SO_2R^d$, $CO_2R^a$, $OC(O)R^a$, $NR^bR^c$, $NR^bC(O)R^a$, $C(O)NR^bR^c$, and $C_{3-8}$ cycloalkyl. In one subset are compounds wherein $R^5$ is $C_{1-3}$ alkyl optionally substituted with 1 to 5 halogen atoms. In a further subset are compounds wherein $R^5$ is selected from $C_{1-3}$ alkyl substituted with 1 to 3 halogen atoms, wherein said halogen is chloro or fluoro. In a further subset are compounds wherein $R^5$ is selected from difluoromethyl, dichloromethyl, chloro-difluoromethyl, trifluoromethyl, 1,1-dichloroethyl and 2,2,2-trifluoroethyl.

In another embodiment of formula I are compounds wherein $R^5$ is pyrimidinyl, 1,2,6-thiadiazolyl, isoxazolyl or isothiazolyl.

For compounds of formula I examples of $R^{6a}$ include 1-methylethyl, 1-hydroxy-ethyl, carboxy, methoxycarbonyl, ethoxycarbonyl, 2-fluoroethoxycarbonyl, isopropoxycarbonyl, phenoxycarbonyl, cyclopentoxycarbonyl, cyclobutoxycarbonyl, cyclopropoxycarbonyl, 2,2,2-trifluoroethoxycarbonyl, 4-trifluoromethylphenoxycarbonyl, methoxyaminocarbonyl, methoxy-carbonylmethyl, formyl, hydroxy, 5-methyl-1,2,4-oxadiazol-3-yl, 3-methyl-1,2,4-oxadiazol-5-yl, 1-methyl-5-tetrazolyl, 2-methyl-5-tetrazolyl, cyano, difluoromethoxy, trifluoromethoxy, 2,2-difluoroethoxy, 1,3-difluoropropoxy, 2,2,2-trifluoroethoxy, trifluoromethyl, chloro, fluoro, methylaminosulfonyl, dimethylaminosulfonyl, methoxycarbonylamino, ethoxycarbonylamino, 2-fluoroethoxycarbonylamino, methylaminocarbonylamino, dimethylamino, methylaminocarbonyl, isopropylaminocarbonyl, ethylaminocarbonyl, cyclopropylaminocarbonyl, cyclobutylamino-carbonyl, dimethylaminocarbonyl, aminocarbonyl and methoxycarbonyloxy; examples for $R^{6b}$ for compounds of formula I include hydrogen, chloro, fluoro and methoxycarbonyl; examples of $R^{6c}$ include hydrogen, chloro, fluoro and methyl.

In one embodiment of formula I are compounds wherein $R^{6a}$ is $CO_2R^a$, $OR^a$, tetrazolyl optionally substituted with $C_{1-4}$ alkyl or oxadiazolyl optionally substituted with $C_{1-4}$ alkyl, $R^{6b}$ is hydrogen or halogen, and $R^{6c}$ is hydrogen or halogen. In one subset $R^{6a}$ is $C_{1-3}$alkoxycarbonyl, $R^{6b}$ is halogen and $R^{6c}$ is hydrogen or halogen. In another subset $R^{6a}$ is 2-methyl-2H-tetrazol-5-yl, $R^{6b}$ is halogen and $R^{6c}$ is hydrogen or halogen. In yet another subset $R^{6a}$ is $C_{1-3}$alkoxy optionally substituted with 1 to 5 halogen atoms, $R^{6b}$ is halogen and $R^{6c}$ is hydrogen or halogen.

For compounds of formula I, examples of $R^{7a}$ or $R^{7b}$ include hydrogen, fluoro, chloro, bromo, cyano, nitro, hydroxy, methoxy, carboxy, methoxycarbonyl, aminocarbonyl, methylaminocarbonyl, methyl, amino, methylamino, dimethylamino, methanesulfonyl, and the like. In one embodiment, $R^{7a}$ and $R^{7b}$ are independently hydrogen or halogen. In one subset therof, $R^{7a}$ is chlorine or fluorine, and $R^{7b}$ is hydrogen.

In another embodiment of formula I are compounds of formula Ia:

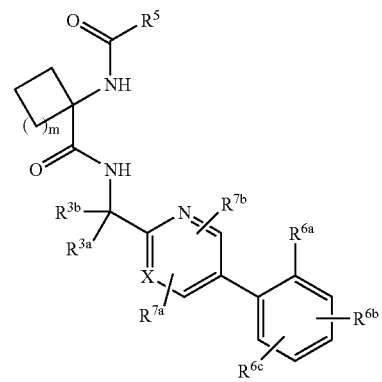

Ia wherein X is carbon or nitrogen, and all other variables are as defined under formula I.

In one subset of formula Ia are compounds where m is 0 or 1. In a second subset of formula Ia are compounds where X is carbon, $R^{7a}$ is hydrogen or chloro or fluoro, and $R^{7b}$ is hydrogen. In a third subset of formula Ia, X is nitrogen and $R^{7a}$ and $R^{7b}$ are each hydrogen. In a fourth subset of formula Ia are compounds where one of $R^{6b}$ and $R^{6c}$ is halogen, and the other is hydrogen or halogen.

In another embodiment of formula I are compounds of formula Ib:

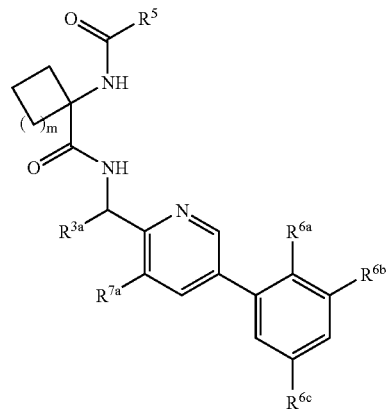

Ib wherein m is 0 or 1, $R^{3a}$ is hydrogen or methyl, $R^{6b}$ and $R^{6c}$ are independently hydrogen, chloro or fluoro, $R^{7a}$ is hydrogen, chloro or fluoro, and the other variables are as defined under formula I.

In one subset of formula Ib are compounds where $R^{3a}$ is hydrogen, and $R^{6b}$ and $R^{7a}$ are each indepedently chloro or fluoro. In a further subset are compounds wherein $R^{3a}$ is hydrogen, $R^{6b}$ and $R^{7a}$ are each indepedently chloro or fluoro, $R^5$ is selected from isoxazolyl, 1,2,5-thiadiazolyl, 5-pyrimidinyl, and $C_{1-2}$alkyl substituted with 1 to 3 halogen atoms selected from chloro and fluoro, and $R^{6a}$ is $OR^a$, $CO_2R^a$ or 2-methyl-5-tetrazolyl. In another subset of formula Ib are compounds where m is 0, $R^5$ is $C_{1-2}$alkyl substituted with 1 to 3 halogen atoms selected from chloro and fluoro and $R^{6a}$ is $CO_2R^a$ or 2-methyl-5-tetrazolyl.

In another embodiment of formula I are compounds of formula Ic:

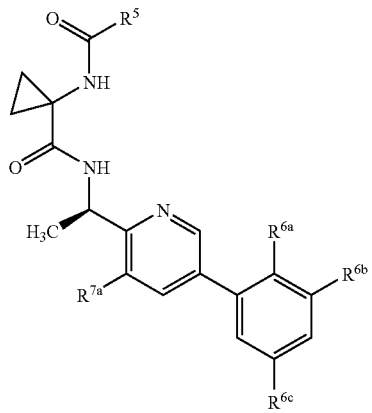

wherein $R^5$, $R^{6a}$, $R^{6b}$, $R^{6c}$ and $R^{7a}$ are as defined under formula I. In one subset of formula Ic are compounds wherein $R^{6b}$ is a halogen atom, and $R^{6c}$ and $R^{7a}$ are independently hydrogen or a halogen atom. In another subset $R^5$ is selected from isoxazolyl, 1,2,5-thiadiazolyl, 5-pyrimidinyl and $C_{1-2}$alkyl substituted with 1 to 5 halogen atoms. In another subset $R^{6a}$ is selected from $CO_2C_{1-4}$alkyl, $C_{1-4}$alkoxy optionally substituted with 1 to 5 halogen atoms and 2-methyl-5-tetrazolyl. In yet another subset of formula Ic are compounds wherein $R^5$ is selected from isoxazolyl, 1,2,5-thiadiazolyl, 5-pyrimidinyl and $C_{1-2}$alkyl substituted with 1 to 5 halogen atoms; $R^{6b}$ is chloro or fluoro; $R^{6c}$ and $R^{7a}$ are independently hydrogen, chloro or fluoro; and $R^{6a}$ is selected from 2-methyl-5-tetrazolyl, $CO_2C_{1-4}$alkyl, and $C_{1-4}$alkoxy optionally substituted with 1 to 5 halogen atoms.

Unless otherwise stated, the following terms have the meanings indicated below:

"Alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec-and tert-butyl, pentyl, hexyl, heptyl and the like.

"Alkenyl" means a linear or branched carbon chain containing at least one C=C bond. Examples of alkenyl include allyl, 2-butenyl, 3-butenyl, 1-methyl-2-propenyl, and the like.

"Alkynyl" means a linear or branched carbon chain containing at least one C≡C bond. Examples of alkynyl include propargyl, 2-butynyl, 3-butynyl, 1-methyl-2-propynyl, and the like.

"Cyclic imide" includes succinimide, maleimide, phthalimide and the like.

"Cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems.

Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydro-naphthalene and the like.

"Haloalkyl" means an alkyl radical as defined above wherein at least one and up to all of the hydrogen atoms are replaced with a halogen. Examples of such haloalkyl radicals include chloromethyl, 1-bromoethyl, fluoromethyl, difluoromethyl, trifluoromethyl, 2,2,2-trifluoroethyl and the like.

"Halogen" means fluorine, chlorine, bromine and iodine.

"Optionally substituted" is intended to include both substituted and unsubstituted. Thus, for example, optionally substituted aryl could represent a pentafluorophenyl or a phenyl ring.

Optical Isomers—Diastereomers—Geometric Isomers—Tautomers

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Salts

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

Prodrugs

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formnula I, additional active ingredient(s), and pharmaceutically acceptable excipients.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |

Water for Injection to a Total Volume of 1 mL

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

Utilities

Compounds of this invention are antagonists or inverse agonists of bradykinin receptor, in particular the bradykinin B1 receptor, and as such are useful in the treatment and prevention of diseases and conditions mediated through the bradykinin receptor pathway such as pain and inflammation. The compounds would be effective in the treatment or prevention of pain including, for example, visceral pain (such as pancreatitis, interstitial cystitis, renal colic), neuropathic pain (such as postherpetic neuralgia, nerve injury, the "dynias", e.g., vulvodynia, phantom limb pain, root avulsions, painful traumatic mononeuropathy, painful polyneuropathy), central pain syndromes (potentially caused by virtually any lesion at any level of the nervous system), and postsurgical pain syndromes (eg, postmastectomy syndrome, postthoracotomy syndrome, stump pain)), bone and joint pain (osteoarthritis), repetitive motion pain, dental pain, cancer pain, myofascial pain (muscular injury, fibromyalgia), perioperative pain (general surgery, gynecological), chronic pain, dysmennorhea, as well as pain associated with angina, and inflammatory pain of varied origins (e.g. osteoarthritis, rheumatoid arthritis, rheumatic disease, tenosynovitis and gout).

Further, the compounds of this invention can also be used to treat hyperreactive airways and to treat inflammatory events associated with airways disease e.g. asthma including allergic asthma (atopic or non-atopic) as well as exercise-induced bronchoconstriction, occupational asthma, viral- or bacterial exacerbation of asthma, other non-allergic asthmas and "wheezy-infant syndrome". Compounds of the present invention may also be used to treat chronic obstructive pulmonary disease including emphysema, adult respiratory distress syndrome, bronchitis, pneumonia, allergic rhinitis (seasonal and perennial), and vasomotor rhinitis. They may also be effective against pneumoconiosis, including aluminosis, anthracosis, asbestosis, chalicosis, ptilosis, siderosis, silicosis, tabacosis and byssinosis.

Compounds of the present invention may also be used for the treatment of inflammatory bowel disease including Crohn's disease and ulcerative colitis, irritable bowel syndrome, pancreatitis, nephritis, cystitis (interstitial cystitis), uveitis, inflammatory skin disorders such as psoriasis and eczema, rheumatoid arthritis and edema resulting from trauma associated with burns, sprains or fracture, cerebral edema and angioedema. They may be used to treat diabetic vasculopathy, diabetic neuropathy, diabetic retinopathy, post capillary resistance or diabetic symptoms associated with insulitis (e.g. hyperglycemia, diuresis, proteinuria and increased nitrite and kallikrein urinary excretion). They may be used as smooth muscle relaxants for the treatment of spasm of the gastrointestinal tract or uterus. Additionally, they may be effective against liver disease, multiple sclerosis, cardiovascular disease, e.g. atherosclerosis, congestive heart failure, myocardial infarct; neurodegenerative diseases, eg. Parkinson's and Alzheimers disease, epilepsy, septic shock e.g. as anti-hypovolemic and/or anti-hypotensive agents, headache including cluster headache, migraine including prophylactic and acute use, closed head trauma, cancer, sepsis, gingivitis, osteoporosis, benign prostatic hyperplasia and hyperactive bladder. Animal models of these diseases and conditions are generally well known in the art, and may be suitable for evaluating compounds of the present invention for their potential utilities. Finally, compounds of the present invention are also useful as research tools (in vivo and in vitro).

The compounds of this invention are useful in the treatment of pain and inflammation by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

The compounds would be effective in the treatment or prevention of pain including, for example, bone and joint pain (osteoarthritis), repetitive motion pain, dental pain, cancer pain, myofascial pain (muscular injury, fibromyalgia), perioperative pain (general surgery, gynecological) and chronic pain by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

In particular, inflammatory pain such as, for example, inflammatory airways disease (chronic obstructive pulmonary disease) would be effectively treated by the compounds of this invention by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Further, the compounds of this invention can additionally be used to treat asthma, inflammatory bowel disease, rhinitis, pancreatitis, cystitis (interstitial cystitis), uveitis, inflammatory skin disorders, rheumatoid arthritis and edema resulting from trauma associated with burns, sprains or fracture by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used subsequent to surgical intervention (e.g. as post-operative analgesics) and to treat inflammatory pain of varied origins (e.g. osteoarthritis, rheumatoid arthritis, rheumatic disease, teno-synovitis and gout) as well as for the treatment of pain associated with angina, menstruation or cancer by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used to treat diabetic vasculopathy, post capillary resistance or diabetic symptoms associated with insulitis (e.g. hyperglycemia, diuresis, proteinuria and increased nitrite and kallikrein urinary excretion) by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used to treat inflammatory skin disorders such as psoriasis and eczema by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used as smooth muscle relaxants for the treatment of spasm of the gastrointestinal tract or uterus or in the therapy of Crohn's disease, ulcerative colitis or pancreatitis by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Such compounds may be used therapeutically to treat hyperreactive airways and to treat inflammatory events associated with airways disease e.g. asthma, and to control, restrict or reverse airways hyperreactivity in asthma by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used to treat intrinsic and extrinsic asthma including allergic asthma (atopic or non-atopic) as well as exercise-induced bronchoconstriction, occupational asthma, viral or bacterial exacerbated asthma, other non-allergic asthmas and "wheezy-infant syndrome" by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may also be effective against pneumoconiosis, including aluminosis, anthracosis, asbestosis, chalicosis, ptilosis, siderosis, silicosis, tabacosis and byssinosis was well as adult respiratory distress syndrome, chronic obstructive pulmonary or airways disease, bronchitis, allergic rhinitis, and vasomotor rhinitis by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Additionally, they may be effective against liver disease, multiple sclerosis, atherosclerosis, Alzheimer's disease, septic shock e.g. as anti-hypovolemic and/or anti-hypotensive agents, cerebral edema, headache including cluster headache, migraine including prophylactic and acute use, closed head trauma, irritable bowel syndrome and nephritis by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to:

(1) morphine and other opiate receptor agonists including propoxyphene (Darvon); (2) non-steroidal antiinflammatory drugs (NSAIDs) including COX-2 inhibitors such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenaric acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone), and the coxibs (celecoxib, valecoxib, rofecoxib and etoricoxib); (3) corticosteroids such as betamethasone, budesonide, cortisone, dexamethasone, hydrocortisone, methylprednisolone, prednisolone, prednisone and triamcinolone; (4) histamnine H1 receptor antagonists such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, desloratadine, fexofenadine and levocetirizine; (5) histamine H2 receptor antagonists such as cimetidine, famotidine and ranitidine; (6) proton pump inhibitors such as omeprazole, pantoprazole and esomeprazole; (7) leukotriene antagonists and 5-lipoxygenase inhibitors such as zafirlukast, montelukast, pranlukast and zileuton; (8) drugs used for angina, myocardial ischemia including nitrates such as nitroglycerin and isosorbide nitrates, beta blockers such as atenolol, metoprolol, propranolol, acebutolol, betaxolol, bisoprolol, carteolol, labetalol, nadolol, oxprenolol, penbutolol, pindolol, sotalol and timolol, and calcium channel blockers such as diltiazam, verapamil, nifedipine, bepridil, felodipine, flunarizine, isradipine, nicardipine and nimodipine; (9) incontinence medications such as antimuscarinics, e.g., tolterodine and oxybutinin); (10) gastrointestinal antispasmodics (such as atropine, scopolamine, dicyclomine, antimuscarinics, as well as diphenoxylate); skeletal muscle relaxants (cyclobenzaprine, carisoprodol, chlorphenesin, chlorzoxazone, metaxalone, methocarbamol, baclofen, dantrolene, diazepam, or orphenadrine); (11) gout medications such as allopurinol, probenicid and colchicine; (12) drugs for rheumatoid arthritis such as methotrexate, auranofin, aurothioglucose and gold sodium thiomalate; (13) drugs for osteoporosis such as alendronate and raloxifene; decongestants such as pseudoephedrine and phenylpropanolamine; (14) local anesthetics; (15) anti-herpes drugs such as acyclovir, valacyclovir and famcyclovir; and (15) anti-emetics such as ondansetron and granisetron.

Biological Evaluation

Assessing the Affinity of Selected Compounds to Bind to the Bradykinin B 1 or B2 Receptor Radioligand binding assays are performed using membranes from CHO cells that stably express the human, rabbit, rat, or dog B1 receptors or CHO cells that express the human B2 receptor. For all receptor types, cells are harvested from culture flasks in PBS/1 mM EDTA and centrifuged at 1000×g for 10 minutes. The cell pellets are homogenized with a polytron in ice cold 20 mM HEPES, 1 mM EDTA, pH 7.4 (lysis buffer) and centrifuged at 20,000×g for 20 minutes. The membrane pellets are rehomogenized in lysis buffer, centrifuged again at 20,000×g and the final pellets are resuspended at 5 mg protein/ml in assay buffer (120 mM NaCl, 5 mM KCl, 20 mM HEPES, pH 7.4) supplemented with 1% BSA and frozen at −80° C.

On the day of assay, membranes are centrifuged at 14,000×g for 5 minutes and resuspended to the desired protein concentration in assay buffer containing 100 nM enaliprilat, 140 µg/mL bacitracin and 0.1% BSA. 3H-des-arg10, leu9 kallidin is the radioligand used for the human and rabbit B1 receptors, 3H-des-arg10 kallidin is used for the rat and dog B1 receptors, and 3H-bradykinin is used to label the human B2 receptor.

For all assays, compounds are diluted from DMSO stock solutions with 4 µL added to assay tubes for a final DMSO concentration of 2%. This is followed by the addition of 100 µL radioligand and 100 µL of the membrane suspension. Nonspecific binding for the B1 receptor binding assays is determined using 1 µM des-arg10 kallidin and nonspecific binding for the B2 receptor is determined with 1 µM bradykinin. Tubes are incubated at room temperature (22° C.) for 60 minutes followed by filtration using a Tomtec 96-well harvesting system. Radioactivity retained by the filter is counted using a Wallac Beta-plate scintillation counter.

The compounds of this invention have affinity for the B1 receptor in the above assay as demonstrated by results of less than 5 µM. It is advantageous that the assay results be less than 1 µM, even more advantageous for the results be less than 0.5 μM. It is further advantageous that compounds of this invention have affinity for the bradykinin B 1 receptor over the bradykinin B2 receptor; more advantageously, the affinity for the B1 receptor is at least 10 fold, and preferably over 100 fold, over that for the B2 receptor.

Assay for Bradykinin B1 Antagonists

B1 agonist-induced calcium mobilization was monitored using a Fluorescence Imaging Plate Reader (FLIPR). CHO cells expressing the B1 receptor were plated in 96 or 384 well plates and allowed to incubate in Iscove's modified DMEM overnight. Wells were washed two times with a physiological buffered salt solution and then incubated with 4 uM Fluo-3 for one hour at 37° C. The plates were then washed two times with buffered salt solution and 100 uL of buffer was added to each well. Plates were placed in the FLIPR unit and allowed to equilibrate for two minutes. The test compound was then added in 50 ul volumes followed five minutes later by 50 ul of agonist (des-arg$^{10}$ kallidin). Relative fluorescence peak heights in the absence and presence of antagonist were used to calculate the degree of inhibition of the B1 receptor agonist response by the test compound. Eight to ten concentrations of test compound were typically evaluated to construct an inhibition curve and determine IC50 values using a four-parameter nonlinear regression curve fitting routine.

Assay for Bradykinin Inverse Agonists

Inverse agonist activity at the human B1 receptor was evaluated using transiently transfected HEK293 cells. One day following transfection cell flasks were labeled overnight with 6 uCi/ml [$^3$H]myo-inositol. On the day of assay, the media was removed and the attached cells were gently rinsed with 2×20 ml of phosphate-buffered saline. Assay buffer (HEPES buffered physiological salts, pH 7.4) was added and the cells were detached by tapping of the flask. The cells were centrifuged at 800×g for five minutes and resuspended at 1×10$^6$ cells/ml in assay buffer supplemented with 10 mM lithium chloride. After 10 minutes at room temperature, one-half ml aliquots were distributed to tubes containing test compound or vehicle. After an additional 10 minutes the tubes were transferred to a 37° C. water bath for 30 minutes. The incubation was terminated by the addition of a 12% perchloric acid solution and the tubes were placed on ice for 30 minutes. The acid was then neutralized with KOH and the tubes centrifuged to pellet precipitated material. [$^3$H]Inositol monophosphate formed was recovered by standard ion exchange chromatographic techniques and quantitated by liquid scintillation counting. Inverse agonist activity was determined by the degree to which a test compound reduced basal (cells incubated with vehicle) levels of [$^3$]inositol monophosphate accumulation.

Abbreviations Used

The following abbreviations have the meanings indicated, unless stated otherwise in the specification:
BOC (boc) t-butyloxycarbonyl
DCM dichloromethane
DEA Diethylamine
DMF dimethylformamide
DMSO Dimethyl sulfoxide
EDC or EDCI 1-(3-dimethylaminopropyl)3-ethylcarbodiimide HCl
eq. equivalent(s)
ES (or ESI)—MS electron spray ionization—mass spectroscopy
Et ethyl
EtOAc ethyl acetate
EtOH ethanol
FAB-MS fast atom bombardment-mass spectroscopy
HOBt 1-hydroxybenzotriazole hydrate
HPLC high pressure liquid chromatography
LCMS Liquid chromatography/mass spectroscopy
LDA Lithium diisopropylamide
LHMDS lithium bis(trimethylsilyl)amide
Me methyl
MeOH Methanol
MHz megahertz
MsCl Mesyl chloride
NEt$_3$ Triethylamine
NMR nuclear magnetic resonance
TFA trifluoroacetic acid
THF tetrahydrofuran Compounds of formula I may be prepared following illustative the schemes and examples.

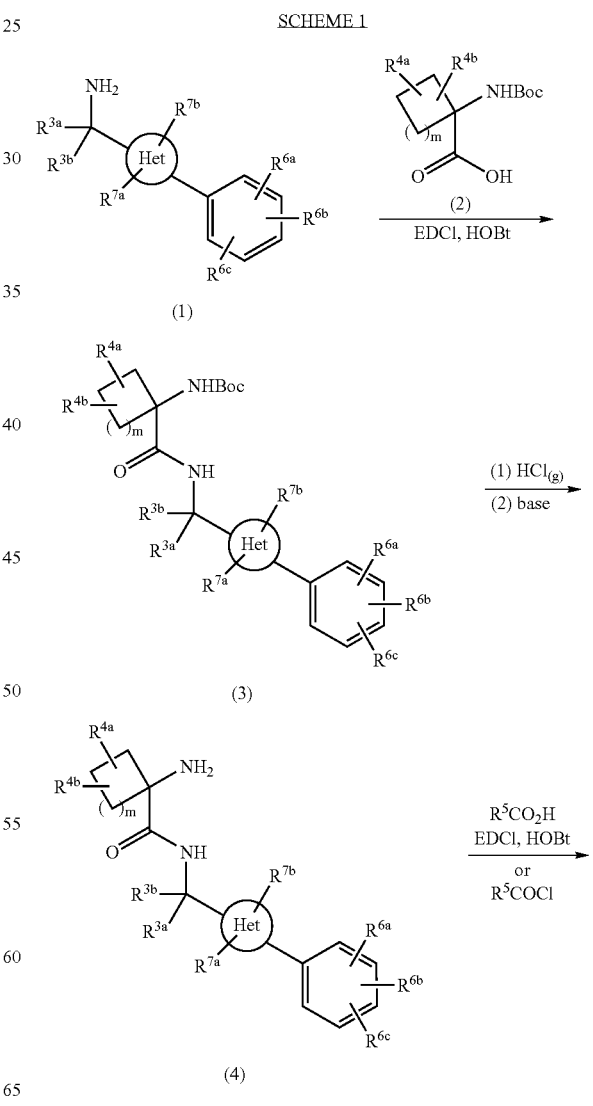

-continued

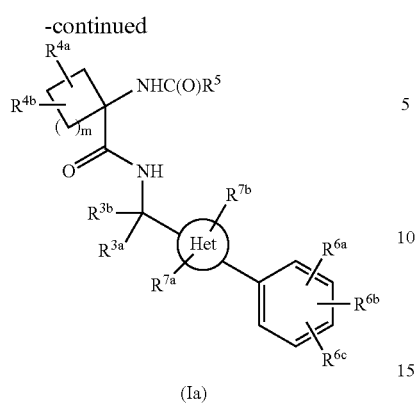

(Ia)

In Scheme 1, compound (Ia) is assembled by coupling the biarylmethanamine derivative (1) to the protected aminocycloalkanoic acid (2) using standard peptide coupling reagent combinations, such as EDCI/HOBt, in an appropriate solvent, such as THF, to provide (3). The Boc protecting group is then removed by the action of an acid, like HCl, in an appropriate solvent, like MeOH, to yield an ammonium salt from which the free-base derivative (4) may be obtained using an-appropriate base, such as ammonia, and an appropriate solvent, such as chloroform. This amine derivative (4) is then reacted with a carboxylic acid or carboxylic acid equivalent to yield title compound (Ia). Alternatively, the acid-salt of (4) can be used in the final reaction to yield title compound (Ia) provided an appropriate base such as triethylamine is added.

Alternatively, compound (Ia) may be assembled by coupling the biarylmethanamine derivative (1), with the acylated aminocycloalkanoic acid (5) as shown in Scheme 1a.

SCHEME 1a

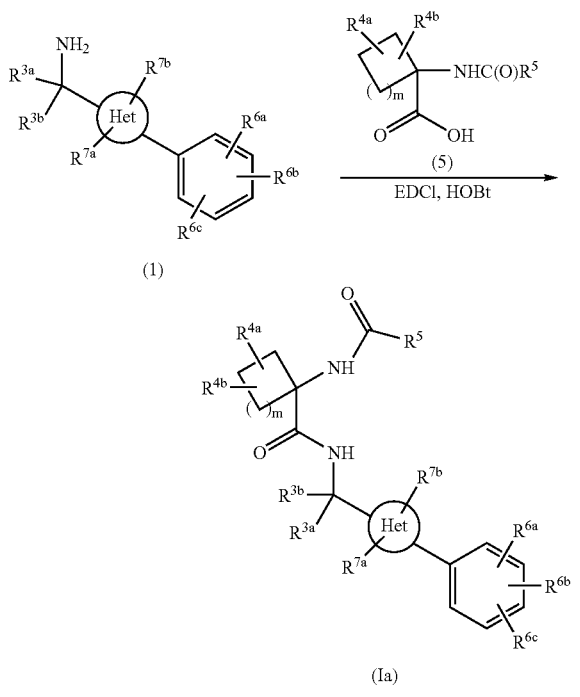

A number of synthetic strategies may be employed to assemble the intermediate biarylmethanamine derivative (1) as shown in Schemes 2a–2c.

SCHEME 2a

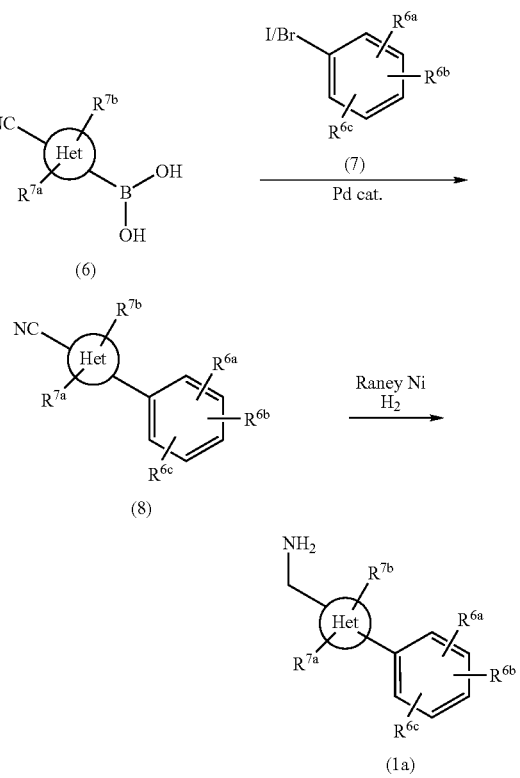

In Scheme 2a, the cyanobiaryl derivative (8) is assembled using a Suzuki reaction between an aromatic boronic acid derivative (6), or an appropriate boronic ester derivative, and an aromatic halide (7) in the presence of a triarylphosphine, like triphenylphosphine, and a metal catalyst, like palladium acetate. The resultant cyano biaryl intermediate (8) is then catalytically reduced to the corresponding amine biaryl derivative (1a) using hydrogen and a metal, such as Raney Ni, in an appropriate solvent.

Alternatively, as illustrated in Scheme 2b, a methanamine derivative (9), after primary amine protection with an appropriate protecting group such as Boc, is elaborated to the pinacol boron ester (11) using a palladium catalyst in an appropriate solvent, like dimethyl sulfoxide. This boron ester (11) is coupled to an aryl halide derivative (7) employing Suzuki reaction conditions to yield (1).

SCHEME 2b

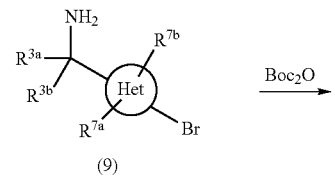

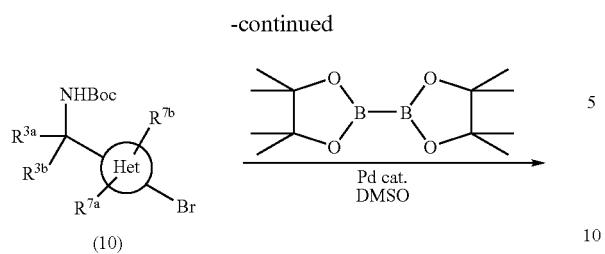

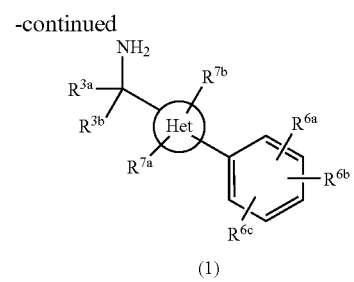

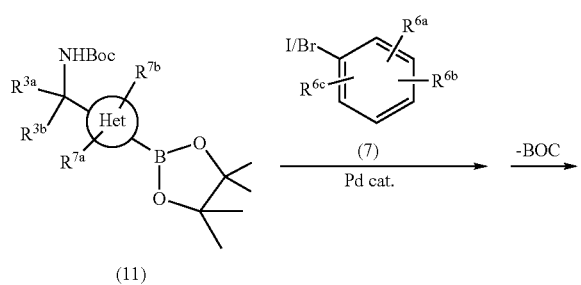

A third method for the preparation of biarylmethanamine derivatives is depicted in Scheme 2c. The biaryl moiety (14) is first assembled using a palladium catalyzed coupling of (12) with an aryl zinc compound (13) as shown. The methyl group of biaryl (14) is then elaborated according to the three step sequence of halogenation, nucleophilic displacement of the halogen with azide, and reduction to provide the corresponding amine intermediate (1a). Alternatively, the biarylmethanamine (1a) can also be prepared starting from the arylcarbonitrile (16) and aryl zinc compound (13) as previously discussed. The resulting biarylcarbonitrile (8) is then reduced using hydrogen to provide (1a).

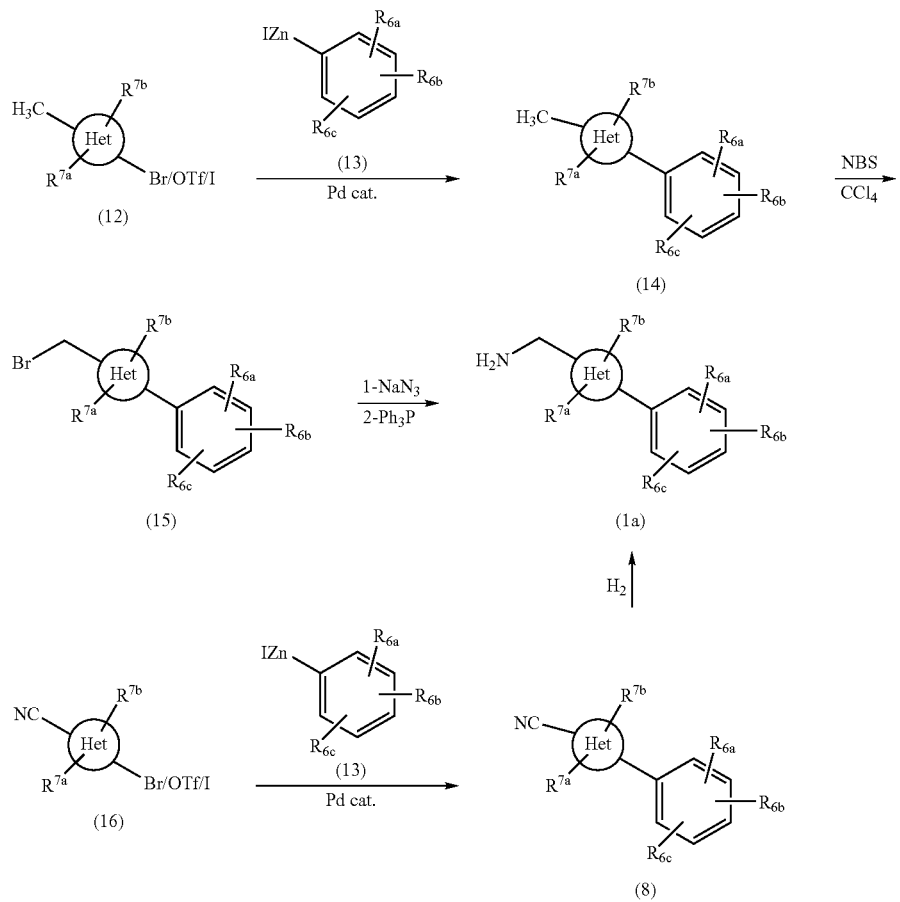

A fourth method for the preparation of biarylmethanamine derivatives is depicted in Scheme 2d. Reduction of the nitro group and nitrile hydrolysis of known pyridine (26) (*J. Chem. Soc*, (1952), 2042–2046.) is followed by conversion of the resultant amine to the fluoride to afford (27). The amide is converted in a 3 step sequence to aldehyde (28). Imine formation with t-butyl sulfinamide is followed by addition of methyl Grignard to produce (30), which may be further elaborated to provide the biarylmethanamine as shown in Scheme 2b.

SCHEME 2d.

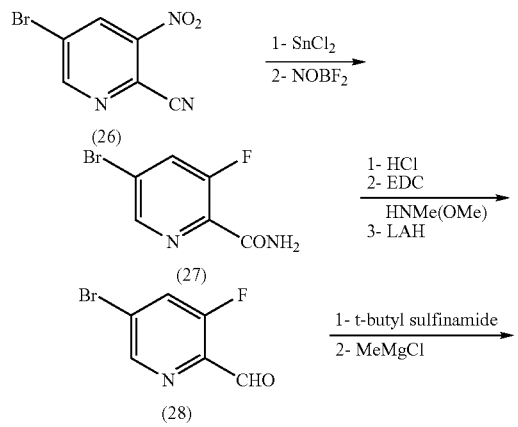

-continued

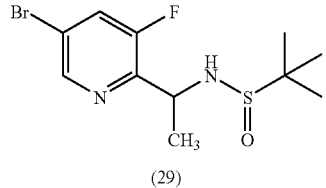

It will be appreciated by persons skilled in the art that functional group interconversion can be used to provide various compounds of formula I. As illustrated in Scheme 3, derivative (3a) is bis-deprotected first by the action of a strong acid, like TFA, and second by alkaline hydrolysis in a suitable mixture of water and an organic solvent, like methanol, at a temperature between 25 and 100° C. to yield the amino acid derivative (17). Prior activation of a carboxylic acid ($R^5COOH$) with an appropriate set of peptide coupling reagents, like EDCI/HOBt, forms the 'active ester' which then reacts with the amino acid derivative (17) to yield (18). The latter compound can either react with amines ($HNR^bR^c$) or alkyloxy amines ($H_2NOR^a$) under the action of an appropriate set of peptide coupling reagents, like EDCI/HOBt, to form the claimed compounds (Ib) and (Ic), respectively.

SCHEME 3

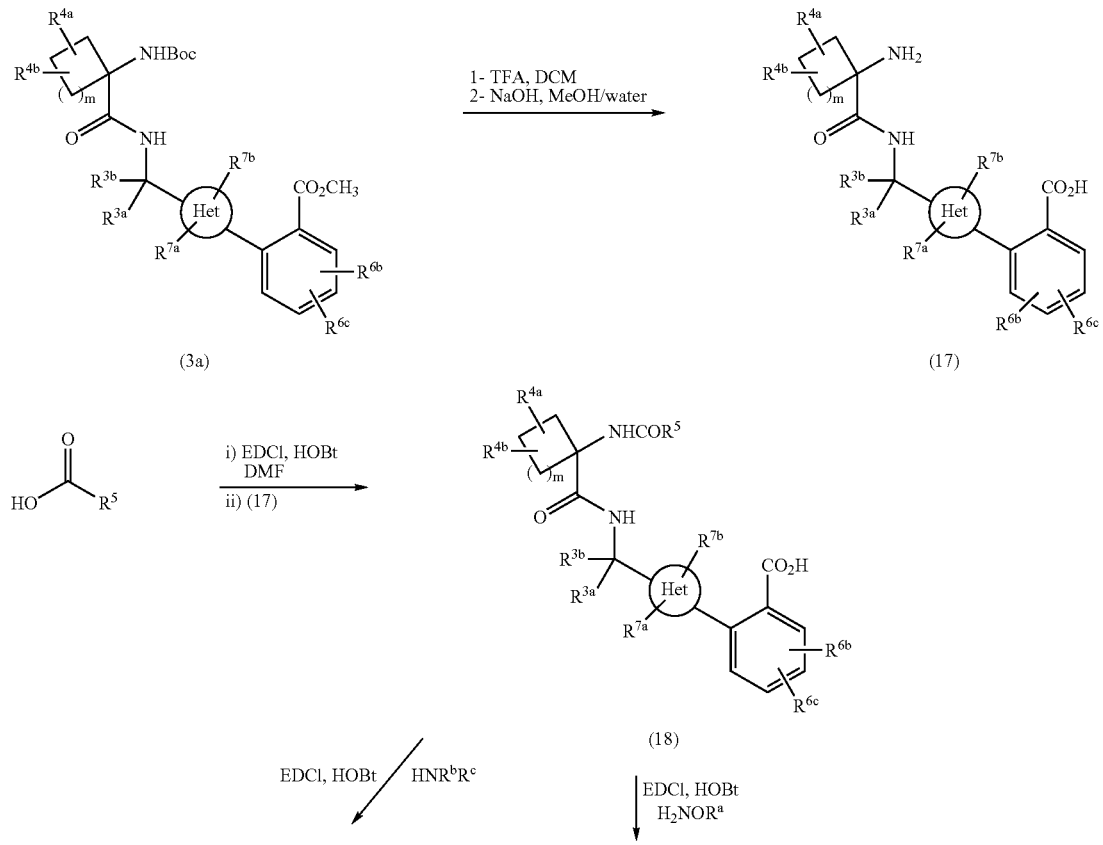

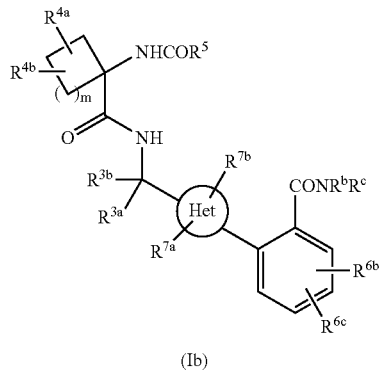

(Ib)

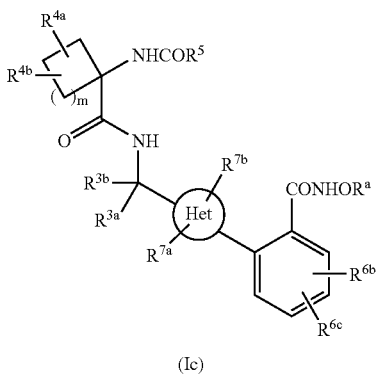

(Ic)

N-alkylation is illustrated in Scheme 4. The amine (4) is alkylated with excess alkyl iodide (I-R$^1$) in an appropriate solvent, like THF, in the presence of an acid scavenger, like triethylamine, at elevated temperatures to provide (19), along with bis-alkylated material. Secondary amine (19) is then converted to the title compound by reacting with a carboxylic acid or carboxylic acid equivalent to provide (Id).

SCHEME 4

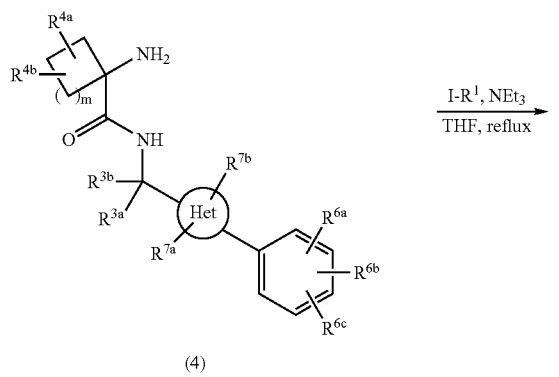

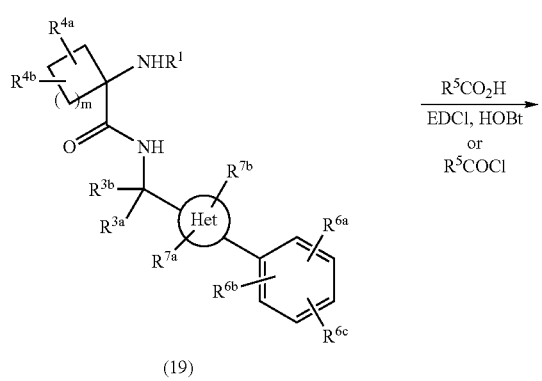

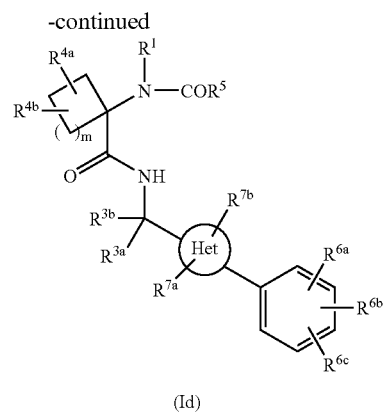

(Id)

The preparation of compounds of formula I having a 1,2-cis- or 1,2-trans-cyclopropyl moiety is illustrated in Schemes 5 and 6. According to known procedures (K. Burgess et al., *J. Org. Chem.*, 57:5931–5936(1992)), di-tert-butyl malonate is elaborated to derivative (20). The N-Boc group is removed using methane sulfonic acid according to L. S. Lin et al. *Tetrahedron Lett.*, 41:7013–7016(2000) to give amine (21). This amine is allowed to react with a carboxylic acid or carboxylic acid equivalent under appropriate peptide coupling conditions to yield (22). The tert-butyl ester is then cleaved with an acid, like TFA, in an appropriate solvent, like DCM, to provide acid (23). Biaryl-methanamine (1) is then coupled with the acid (23) using an appropriate set of peptide coupling reagents, like EDCI/HOBt, to produce the title compound (Ie). Further elaboration of (Ie) to additional compounds of formula I may be accomplished using procedures well known to those skilled in the art. For example, the acetyl group may be removed by hydrolysis to provide the corresponding alcohol; the alcohol may be converted to the corresponding sulfonate by treatment with sulfonyl chloride, and the sulfonate may be converted to the corresponding halide by treatment with a source of the halide. These and other functional transformations to provide compounds of formula I are described in typical organic chemistry textbooks such as March's Advanced Organic Chemistry: Reactions, Mechanisms, and Structure, 5$^{th}$ Ed., John Wiley & Sons, 2000.

SCHEME 5

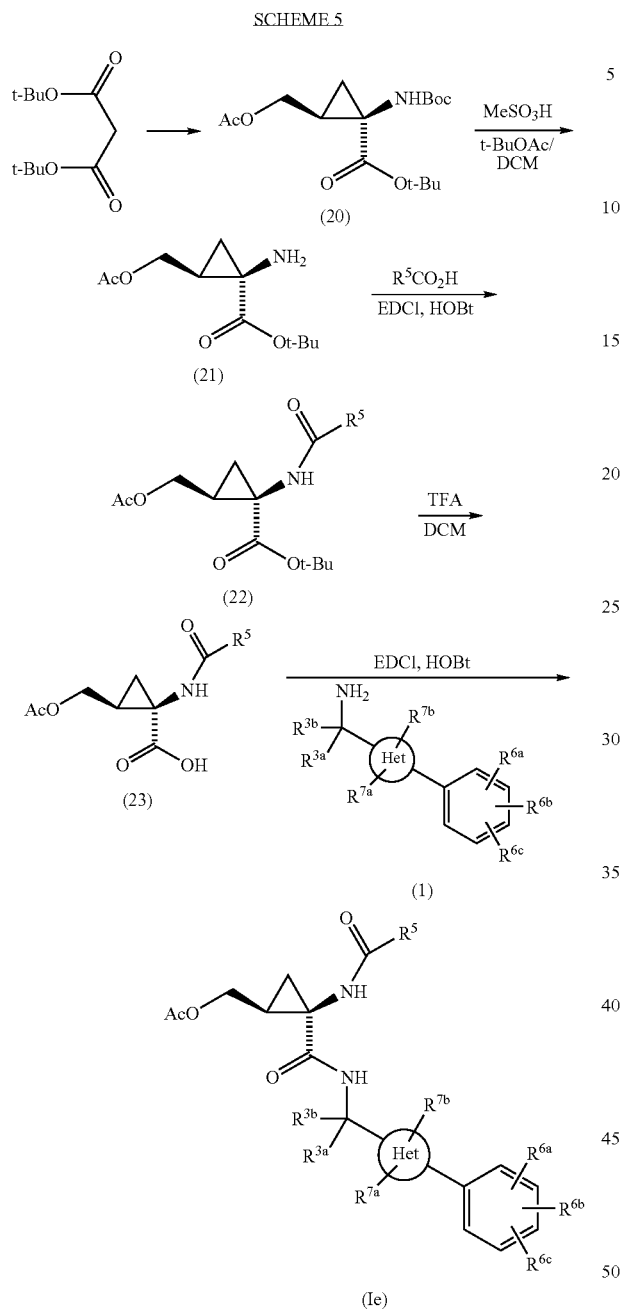

SCHEME 6

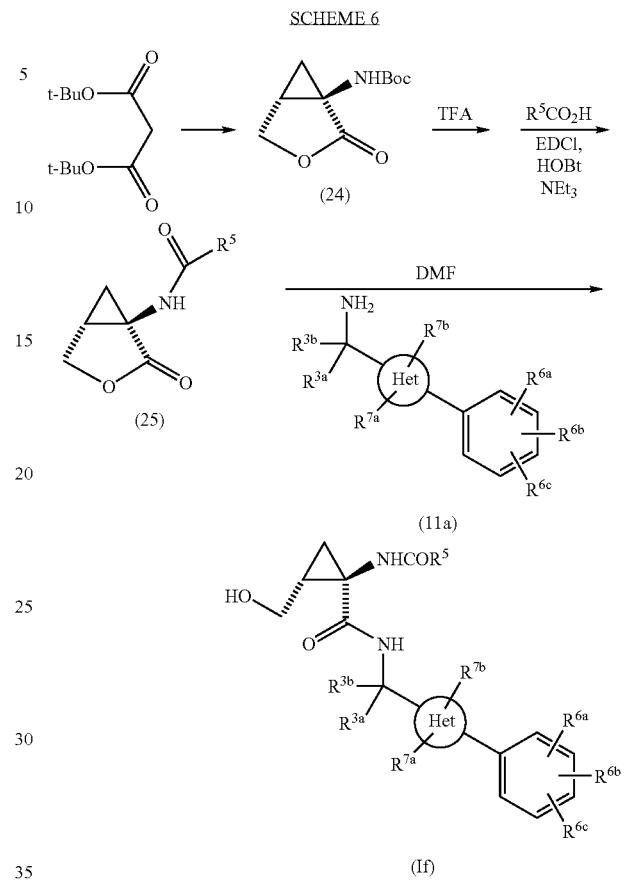

In Scheme 6, according to known procedures (K. Burgess et al., *J. Org. Chem.*, 57:5931–5936(1992)), di-tert-butyl malonate is elaborated to derivative (24). The N-Boc group is removed using an acid, like TFA, in an appropriate solvent, like DCM. This amine is allowed to react with a carboxylic acid or carboxylic acid equivalent under appropriate peptide coupling conditions, like EDCI/HOBt/NEt₃ to yield (25). Biarylmethanamine (1), is then allowed to open the lactone (25) in an appropriate aprotic solvent, like DMF, at a temperature between 20 and 100° C., to produce the title compound (If). Further elaboration of (If) to additional title compounds may be accomplished using procedures well known to those skilled in the art as previously discussed.

The following examples are provided to illustrate the invention without limiting the invention to the particulars of these examples. Compounds were named using: ACD/Name version 4.53 (Advanced Chemistry Development Inc.© 1994–2000). Address: 90 Adelaide Street West, Toronto, Ontario, M5H 3V9, Canada.

EXAMPLE 1

Methyl 2-fluoro-6-(2-{[({1-[(pyrimidin-5-ylcarbonyl)amino]cyclobutyl}carbonyl)-amino]-methyl}pyrimidin-5-yl)benzoate

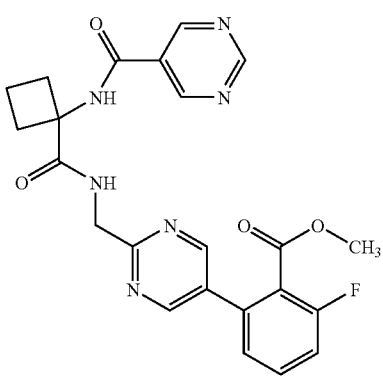

Sodium azide (3.14 g, 48.3 mmol) was partially dissolved in dry DMSO (50 mL), under nitrogen at ambient temperature. Ethyl 1-bromocyclobutanecarboxylate (3.91 mL, 24.2 mmol, Aldrich) was then added via syringe. After heating to 40° C. for 7 hours, the homogenous solution was allowed to cool to ambient temperature and stirring was continued overnight. The reaction mixture was then poured into water (700 mL), along with diethyl ether (200 mL). The ether layer was washed three times with half brine and then once with brine. The organic layer was dried over sodium sulfate, filtered and then evaporated under reduced pressure to provide ethyl 1-azidocyclobutanecarboxylate (4.00 g) as a clear oil.

Ethyl 1-azidocyclobutanecarboxylate (4.00 g, 23.6 mmol) was dissolved in methanol (150 mL) under nitrogen. Palladium on carbon (840 mg, 10% wt/wt) was then added prior to exchanging the nitrogen for hydrogen. After 3 hours the reaction was judged complete (LCMS). The reaction mixture was filtered through celite and the celite was washed with additional methanol. The combined methanolic solutions were made acidic by the addition of HCl (2.0 M in diethyl ether), prior to removal of the solvents under reduced pressure. The ethyl 1-aminocyclobutane-carboxylate hydrochloride thus obtained (4.70 g) slowly solidifies into a low melting waxy solid that retains a fair amount of methanol, as determined by proton NMR.

To a room temperature, stirred solution of the above mentioned amine hydrochloride (1.03 g, 5.73 mmol) in DMF (30.0 mL) was added HOBt.$H_2O$ (0.879 g, 5.73 mmol), pyrimidine-5-carboxylic acid (0.783 g, 6.31 mmol), EDCI (1.21 g, 6.31 mmol) and lastly triethylamine (1.60 mL, 11.5 mmol). After overnight stirring (ca. 15 h) most of the solvent was removed under reduced pressure. The residue was then diluted with EtOAc and 5% aqueous sodium bicarbonate. This aqueous layer was extracted twice with EtOAc. The combined organics were washed with saturated copper (II) sulfate, half brine (twice) and then brine. The organic layer was dried over sodium sulfate, filtered and evaporated under reduced pressure to obtain a residue, which was subject to silica gel chromatography. Collection of the product containing fractions and removal of solvent yielded ethyl 1-[(pyrimidin-5-ylcarbonyl)amino]-cyclobutanecarboxylate (0.939 g) as a white crystalline solid, giving proton NMR and LC/MS data consistent with theory.

Ethyl 1-[(pyrimidin-5-ylcarbonyl)amino]cyclobutanecarboxylate (0.939 g, 3.77 mmol) was dissolved in THF (36.0 mL) prior to addition of aqueous sodium hydroxide (6.03 mL, 1M). The reaction mixture was then allowed to stir over the weekend (ca. 64 h) at ambient temperature. Most of the THF was then removed under reduced pressure to yield an oily aqueous layer, which was diluted with additional water, prior to three-fold extraction with diethyl ether. The aqueous layer was then made neutral by the addition of HCl (6.00 mL, 1H) and then saturated with sodium chloride. Repeated extraction of this aqueous layer with EtOAc (ca. 500 mL total) followed by concentration of the organic layers provided 1-[(pyrimidin-5-ylcarbonyl)-amino]cyclobutanecarboxylic acid (0.756 g) as a white solid giving proton NMR and LC/MS data consistent with theory.

To a room temperature DMSO solution (20.0 mL) of 5-bromo-2-chloropyrimidine (1.02 g, 5.27 mmol) was added sodium cyanide (0.284 g, 5.80 mmol). After 70 minutes the reaction mixture was diluted with water (300 mL) and EtOAc (150 mL). The organic layer was washed three times with half brine, then once with brine. The organic layer was dried over sodium sulfate, filtered and evaporated under reduced pressure to obtain a residue, which was subject to silica gel chromatography. Collection of the product containing fractions and removal of solvent provided 5-bromopyrimidine-2-carbonitrile (0.800 g) as a white crystalline solid, giving proton NMR and LC/MS data consistent with theory.

Rieke zinc (5.0 g, 76 mmol, Aldrich) in THF (100 mL) was transferred into a dry reaction vessel, followed by methyl 2-fluoro-6-iodobenzoate (16.1 g, 57.5 mmol) in THF (15 mL). The heterogeneous mixture was then refluxed under nitrogen for 1 hour (LC/MS indicated complete consumption of starting iodide) to form an approximately 0.43 M solution of [3-fluoro-2-(methoxycarbonyl)phenyl](iodo)zinc in THF. A portion of this solution (5.6 mL, 2.4 mmol) was then added to a dry flask already containing 5-bromopyrimidine-2-carbonitrile (0.40 g, 2.2 mmol) and tetrakis(triphenylphosphine)palladium(0) (0.13 g, 0.11 mmol). After refluxing this mixture for 30 minutes the reaction was judged complete (LC/MS) and allowed to cool to ambient temperature. The reaction mixture was diluted with water and EtOAc. The organic layer was washed twice with water and then once with brine, prior to drying over sodium sulfate. The dried solution was filtered and then evaporated under reduced pressure to obtain a residue, which was subject to silica gel chromatography. Collection of the product containing fractions and removal of solvent provided methyl 2-(2-cyanopyrimidin-5-yl)-6-fluorobenzoate (0.37 g) as a white solid, giving proton NMR and LC/MS data consistent with theory.

Methyl 2-(2-cyanopyrimidin-5-yl)-6-fluorobenzoate (100 mg, 0.389 mmol) was dissolved in methanol (4.0 mL) under nitrogen. Palladium on carbon (840 mg, 10% wt/wt) and concentrated HCl (32 μL) were then added prior to exchanging the nitrogen for hydrogen. After 30 minutes the reaction was judged complete (LCMS). The reaction mixture was filtered through celite and the celite was washed with additional methanol. Removal of the solvent under reduced pressure provided methyl 2-[2-(aminomethyl)pyrimidin-5-yl]-6-fluorobenzoate hydrochloride (104 mg) of 90% pure material, as determined by proton NMR and LCMS.

To a room temperature, stirred solution of the above mentioned amine hydrochloride (104 mg, 0.353 mmol) in DMF (3.5 mL) was added HOBt.$H_2O$ (59.6 mg, 0.39 mmol), 1-[(pyrimidin-5-ylcarbonyl)amino]cyclobutanecarboxylic acid (85.9 mg, 0.39 mmol), EDCI (81.2 g, 0.42 mmol) and lastly triethylamine (0.10 mL, 0.71 mmol). After overnight stirring (ca. 15 h) the reaction mixture was diluted with water (70 mL), EtOAc (80 mL) and aqueous 5% sodium bicarbonate (ca. 5 mL). The organic layer was washed with saturated copper (II) sulfate, half brine (three times) and then brine. The organic layer was dried over sodium sulfate, filtered and evaporated under reduced pressure to obtain a residue which was subject to silica gel chromatography eluting with 1–10% MeOH in DCM. Collection of product containing fractions and removal of solvent yielded 53.4 mg (33%) of the title compound as a foaming solid. Purity was determined by LCMS (ES MS, M+H$^+$found:465) and proton NMR (400 MHz, $CD_3OD$: δ 9.287, 9.243, 8.669, 7.669, 7.655, 7.650, 7.648, 7.636, 7.634, 7.629, 7.615, 7.360, 7.358, 7.377, 7.334, 7.315, 7.297, 7.296, 4.662, 3.712, 2.866, 2.849, 2.845, 2.841, 2.833, 2.829, 2.820, 2.815, 2.797, 2.464, 2.443, 2.421, 2.412, 2.408, 2.389, 2.088, 2.067, 2.048, 2.043).

EXAMPLE 2

N-({3-chloro-5-[3-fluoro-2-(2-methyl-2H-tetrazol-5-yl)phenyl]pyridin-2-yl}methyl)-1-[(trifluoroacetyl)amino]cyclopropanecarboxamide

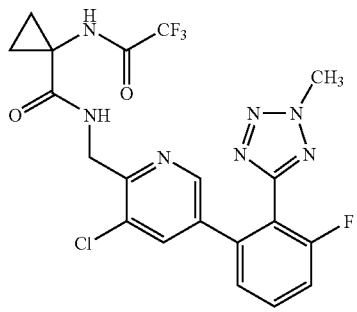

A solution of 2-fluoro-6-iodobenzonitrile (17.82 g, 72.15 mmol) and azidotrimethyltin (15.00 g, 72.88 mmol) in 150 mL toluene was heated to 125° C. for 72 hours. The solution was cooled to room temperature and partitioned between ethyl acetate and 0.5 N HCl. The organic extract was washed with water and brine, dried over $Na_2SO_4$, filtered and concentrated under vacuum to provide 5-(2-fluoro-6-iodophenyl)-1H-tetrazole that gave proton NMR spectra consistent with theory and a mass ion (ES+) of 291.01 for M+H$^+$.

A mixture of 5-(2-fluoro-6-iodophenyl)-1H-tetrazole (23.48 g, 80.97 mmol), potassium carbonate (16.79 g, 0.121 mol), and iodomethane (16.09 g, 0.113 mol) in 25 mL DMF was stirred at room temperature for 3 hours. The mixture was partitioned between ethyl acetate and water, and the organic extract was washed with water and brine, dried over $Na_2SO_4$, filtered and concentrated under vacuum. The residue was subjected to silica gel chromatography eluted with 0–10% ethyl acetate in hexanes to provide 5-(2-fluoro-6-iodophenyl)-2-methyl-2H-tetrazole that gave proton NMR spectra consistent with theory and a mass ion (ES+) of 305.06 for M+H$^+$.

A mixture of 5-chloropyridin-3-yl trifluoromethanesulfonate (6.00 g, 22.9 mmol), bis(pinacolato)diboron (6.12 g, 24.1 mmol), potassium acetate (6.75 g, 68.8 mmol), and [1,1'-bis-(diphenylphosphino)ferrocene]palladium(II) dichloride (0.60 g, 0.82 mmol) in 30 mL DMF was heated to 80° C. under $N_2$ for 2 hours. The reaction mixture was cooled to room temperature, and 5-(2-fluoro-6-iodophenyl)-2-methyl-2H-tetrazole (4.88 g, 16.1 mmol), sodium bicarbonate (2M, 34.4 mL, 68.8 mmol), and [1,1'-bis(diphenylphosphino)ferrocene]palladium(II) dichloride (0.60 g, 0.82 mmol) were added. The reaction mixture was heated to 80° C. overnight, then cooled to room temperature and partitioned between ethyl acetate and water. The organic extract was washed with water and brine, dried over $Na_2SO_4$, filtered and concentrated under vacuum. The residue was subjected to silica gel chromatography eluted with 0–30% ethyl acetate in hexanes to provide 3-chloro-5-[3-fluoro-2-(2-methyl-2H-tetrazol-5-yl)phenyl]pyridine that gave proton NMR spectra consistent with theory and a mass ion (ES+) of 290.11 for M+H$^+$.

A mixture of 3-chloro-5-[3-fluoro-2-(2-methyl-2H-tetrazol-5-yl)phenyl]pyridine (2.90 g, 9.98 mmol) and 3-chloroperoxybenzoic acid (2.238 g, 12.97 mmol) in 40 mL $CH_2Cl_2$ was stirred at room temperature overnight. Additional 3-chloroperoxybenzoic acid (861 mg, 4.99 mmol) was added in the morning to drive the reaction to completion. The solution was washed with 0.5 N NaOH and brine, dried over $Na_2SO_4$, filtered and concentrated under vacuum to provide 3-chloro-5-[3-fluoro-2-(2-methyl-2H-tetrazol-5-yl)phenyl]pyridine 1-oxide that gave proton NMR spectra consistent with theory and a mass ion (ES+) of 306.13 for M+H$^+$.

To a solution of 3-chloro-5-[3-fluoro-2-(2-methyl-2H-tetrazol-5-yl)phenyl]-pyridine 1-oxide (1.835 g, 5.983 mmol) and triethylamine (1.816 g, 17.95 mmol) in 10 mL DMF was added trimethylsilyl cyanide (1.781 g, 17.95 mmol). The reaction mixture was heated to 80° C. for 3 hours (added another 0.592 g, 2.98 mmol TMS-CN at this point and let stir another hour), then cooled to room temperature and partitioned between ethyl acetate and water. The organic extract was washed with water and brine, dried over $Na_2SO_4$, filtered and concentrated under vacuum to provide crude 3-chloro-5-[3-fluoro-2-(2-methyl-2H-tetrazol-5-yl)phenyl]-pyridine-2-carbonitrile that gave proton NMR spectra consistent with theory and a mass ion (ES+) of 315.14 for M+H$^+$. The $^1$H NMR also shows that the isomeric 5-chloro-3-[3-fluoro-2-(2-methyl-2H-tetrazol-5-yl)phenyl]pyridine-2-carbonitrile was present in about 20%. This would be separated out in a later step.

To a solution of 3-chloro-5-[3-fluoro-2-(2-methyl-2H-tetrazol-5-yl)phenyl]-pyridine-2-carbonitrile (0.500 g, 1.59 mmol) in ammonium in methanol (40 mL 2.0 M) was added Raney 2800 nickel (slurry in water). The reaction mixture was stirred under $H_2$ atmosphere for 3 hours, filtered through glass filter paper and concentrated under vacuum. The residue was azeotroped three times with toluene to yield crude 1-{3-chloro-5-[3-fluoro-2-(2-methyl-2H-tetrazol-5-yl)phenyl]pyridin-2-yl}methanamine that gave a mass ion (ES+) of 319.18 for M+H$^+$.

A solution of 1-{3-chloro-5-[3-fluoro-2-(2-methyl-2H-tetrazol-5-yl)phenyl]-pyridin-2-yl}methanamine (0.639 g, 2.01 mmol), Boc-1-aminocyclopropanecarboxylic acid (0.424 g, 2.11 mmol), 1-ethyl-(3-dimethylaminopropyl)carbodiimide carboxylic acid (0.769 g, 4.01 mmol), 1-hydroxy-7-azabenzotriazole (0.010 g, 0.15 mmol), and triethylamine (1.22 g, 12.0 mmol) in 15 mL $CH_2Cl_2$ was stirred at room temperature for 5 hours. The solution was washed with aqueous sodium bicarbonate and brine, dried over $Na_2SO_4$, filtered and concentrated. The residue was subjected to silica gel chromatography eluted with 10–50% ethyl acetate in hexanes to provide tert-butyl 1-{[({3-chloro-5-[fluoro-2-(2-methyl-2H-tetrazol-5-yl)phenyl]pyridin-2-yl}-methyl)amino]carbonyl}cyclopropylcarbamate that gave proton NMR spectra consistent with theory and a mass ion (ES+) of 502.28 for M+H$^+$. The compound was further purified on a Chiralpak AD column 15–30% isopropanol/hexane (containing 0.1% DEA) to remove tert-butyl 1-{[({5-chloro-3-[3-fluoro-2-(2-methyl-2H-tetrazol-5-yl)phenyl]pyridin-2-yl}methyl)amino]-carbonyl}cyclopropylcarbamate, the side product resulting from the TMSCN step. The product was dissolved in ethyl acetate and saturated with HCl gas. The solution was concentrated in vacuo and azeotroped three times with toluene to provide 2-({[(1-ammoniocyclopropyl)-carbonyl]amino}-methyl)-3-chloro-5-[3-fluoro-2-(2-methyl-2H-tetrazol-5-yl)phenyl]pyridinium dichloride that gave a mass ion (ES+) of 402.23 for M+H$^+$.

To a solution of 2-({[[(1-ammoniocyclopropyl)carbonyl]amino}methyl)-3-chloro-5-[3-fluoro-2-(2-methyl-2H-tetrazol-5-yl)phenyl]pyridinium dichloride (0.390 g, 0.821 mmol) in 5 mL $CH_2Cl_2$ at 0° C. was added triethylamine (0.249 g, 2.46 mmol) and trifluoroacetic anhydride (0.17 g, 0.82 mmol). The solution was diluted with additional CH$_2$Cl$_2$ and washed with aqueous sodium bicarbonate and brine, dried over Na$_2$SO$_4$, filtered and concentrated. The residue was subjected to silica gel chromatography eluted with 0–2% methanol in CH$_2$Cl$_2$ to provide N-({3-chloro-5-[3-fluoro-2-(2-methyl-2H-tetrazol-5-yl)phenyl]pyridin-2-yl}methyl)-1-[(trifluoroacetyl)amino]cyclopropanecarboxamide that gave proton NMR spectra consistent with theory and a mass ion (ES+) of 498.2 for M+H$^+$: $^1$H NMR (300 MHz, MeOH-d$_4$) δ 8.13 (d, J=2.0 Hz, 1H), 7.75–7.68 (m, 2H), 7.45–7.39 (m, 2H), 4.58 (s, 2H), 4.35 (s, 3H), 1.56–1.52 (m, 2H), 1.14 (m, 2H).

EXAMPLE 3

Methyl 2-fluoro-6-(5-fluoro-6-{[({1-[(trifluoroacetyl)amino]cyclopropyl}carbonyl)-amino]methyl}pyridin-3-yl)benzoate

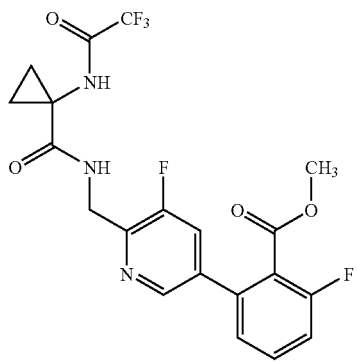

A solution of LDA (40.9 mmol, prepared from 11.4 mL of diisopropyl amine and 16.4 mL of 2.5 M n-butyl lithium in hexanes) in 200 mL THF at −78° C. was treated with 2-cyano-3-fluoropyridine (5.0 g, 40.9 mmol) in 50 mL of THF drop-wise. After 10 minutes a solution of iodine (10.4 g, 40.9 mmol) in 10 mL of TBF was added. After 30 minutes the reaction was quenched with 40 mL of water followed by workup with aqueous sodium thiosulfate. The mixture was diluted with ether, washed with brine, dried over Na$_2$SO$_4$, filtered and concentrated under vacuum. The residue was subjected to silica gel chromatography eluted with 0–20% ethyl acetate in hexanes to provide 3-fluoro-4-iodopyridine-2-carbonitrile that gave proton NMR spectra consistent with theory.

A solution of LDA (16.9 mmol) in 200 mL TBF at −78° C. was treated with 3-fluoro-4-iodopyridine-2-carbonitrile (4.2 g, 16.9 mmol) in 50 mL of TIHF drop-wise. After 2 hours the reaction was quenched with water and warmed to room temperature. The mixture was diluted with ether, washed with brine, dried over Na$_2$SO$_4$, filtered and concentrated under vacuum. The residue was subjected to silica gel chromatography eluted with 0–20% ethyl acetate in hexanes to provide 3-fluoro-5-iodopyridine-2-carbonitrile that gave proton NMR spectra consistent with theory.

A solution of 3-fluoro-5-iodopyridine-2-carbonitrile (1.08 g, 3.87 mmol) in 10 mL of THF and palladium tetrakistriphenylphosphine (0.18 g, 0.16 mmol) was added to a solution of [3-fluoro-2-(methoxycarbonyl)phenyl](iodo)zinc (prepared from methyl 2-fluoro-6-iodobenzoate and Reike Zinc) in 20 mL of THF via cannula. The mixture was heated to reflux for one hour, cooled, and partitioned between ethyl acetate and water. The organic extract was washed with brine, dried over MgSO$_4$, filtered and concentrated under vacuum. The residue was subjected to silica gel chromatography eluted with 0–20% ethyl acetate in hexanes to provide methyl 2-(6-cyano-5-fluoropyridin-3-yl)-6-fluorobenzoate that gave proton NMR spectra consistent with theory.

To a stirred solution of methyl 2-(6-cyano-5-fluoropyridin-3-yl)-6-fluorobenzoate (0.75 g, 2.7 mmol) in NH$_3$/MeOH (5 mL, 2.0 M) was added Raney 2800 nickel (slurry in water). The mixture was stirred under a H$_2$ atmosphere (balloon) at room temperature for 6 hours. The mixture was then filtered through glass filter paper, washing with additional MeOH. The resultant solution was concentrated under vacuum and azeotroped three times with toluene. The crude methyl 2-[6-(aminomethyl)-5-fluoropyridin-3-yl]-6-fluorobenzoate (0.65 g, 2.34 mmol), Boc-1-aminocyclopropane-1-carboxylic acid (0.61 g, 3.04 mmol), 1-ethyl-(3-dimethylamino-propyl)carbodiimide hydrochloride (0.58 g, 3.04 mmol), 1-hydroxy-7-azabenzotriazole (0.010 g, 0.15 mmol), and triethylamine (0.42 mL, 3.04 mmol) in 5 mL DMF was stirred at room temperature for 2 hours. The solution was washed with aqueous sodium bicarbonate and brine, dried over Na$_2$SO$_4$, filtered and concentrated. The residue was subjected to silica gel chromatography eluted with 40–65% ethyl acetate in hexanes to provide methyl 2-(6-{([({1-[(tert-butoxycarbonyl)amino]cyclopropyl}carbonyl)amino]methyl}-5-fluoropyridin-3-yl)-6-fluoro-benzoate that gave proton NMR spectra consistent with theory and a mass ion (ES+) of 462.2 for M+H$^+$.

The above product was dissolved in EtOAc and saturated with HCl gas. The solution was concentrated in vacuo to provide 2-({[(1-ammoniocyclo-propyl)carbonyl]amino}-methyl)-3-fluoro-5-[3-fluoro-2-(methoxycarbonyl)phenyl]-pyridinium dichloride that gave a mass ion (ES+) of 362.2 for M+H$^+$.

To a solution of the above compound (0.110 g, 0.277 mmol) in 5 mL CH$_2$Cl$_2$ at 0° C. was added triethylamine (1.08 g, 1.08 mmol) and trifluoroacetic anhydride (0.4 mL, 0.30 mmol). The solution was diluted with additional CH$_2$Cl$_2$ and washed with aqueous sodium bicarbonate and brine, dried over Na$_2$SO$_4$, filtered and concentrated. The residue was subjected to silica gel chromatography eluted with 20–60% ethyl acetate in hexanes to provide the title compound that gave proton NMR spectra consistent with theory and a mass ion (ES+) of 458.1 for M+H$^+$: $^1$H NMR (300 MHz, MeOH-d$_4$) δ 8.34 (s, 1 H), 7.71–7.60 (m, 2 H), 7.36–7.30 (m, 2 H), 4.63 (d, J=1.5 Hz, 2 H), 3.72 (s, 3 H), 1.54 (m, 2 H), 1.13 (m, 2 H).

The following compounds in Table I were prepared by methods analogous to those described in Example 2 or Example 3, using the commercially available 1-[(tert-butoxy-carbonyl)amino]cyclobutanecarboxylic acid instead of 1-[(tert-butoxycarbonyl)amino]-cyclopropanecarboxylic acid.

TABLE 1

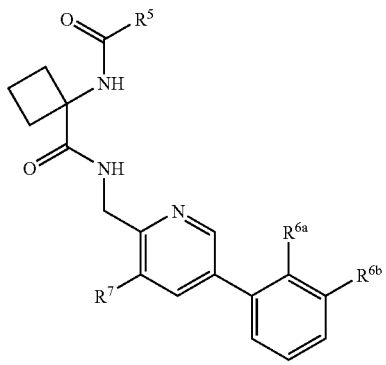

| Example | R$^5$ | R$^{6a}$ | R$^{6b}$ | R$^7$ | ES MS, M + H$^+$ |
|---|---|---|---|---|---|
| 4 | pyrimidin-5-yl | CO$_2$Me | F | Cl | 497 |
| 5 | pyrimidin-5-yl | CO$_2$Me | F | F | 482 |
| 6 | trifluoromethyl | CO$_2$Me | F | F | 472 |
| 7 | trifluoromethyl | 2-methyl-2H-tetrazol-5-yl | F | Cl | 512 |
| 8 | chlorodifluoromethyl | 2-methyl-2H-tetrazol-5-yl | F | Cl | 528 |

The following compounds in Table 2 were prepared by methods analogous to described in Example 2 and Example 3.

TABLE 2

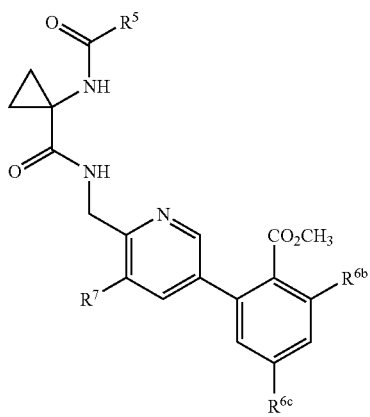

| Example | R$^5$ | R$^{6b}$ | R$^{6c}$ | R$^7$ | M + H$^+$ |
|---|---|---|---|---|---|
| 9 | pyrimidin-5-yl | F | H | F | 468 |
| 10 | pynmidin-5-yl | F | H | Cl | 484 |
| 11 | 2,2,2-trifluoroethyl | F | H | F | 472 |
| 12 | dichloromethyl | F | H | F | 473 |
| 13 | trifluoromethyl | F | H | Cl | 474 |
| 14 | 1,1-dichloroethyl | F | H | Cl | 503 |
| 15 | chlorodifluoromethyl | F | H | F | 474 |
| 16 | chlorodifluoromethyl | F | H | Cl | 491 |
| 17 | trifluoromethyl | Cl | H | Cl | 490 |
| 18 | difluoromethyl | Cl | H | Cl | 472 |
| 19 | chlorodifluoromethyl | Cl | H | Cl | 506 |
| 20 | trifluoromethyl | Cl | H | F | 472 |

TABLE 2-continued

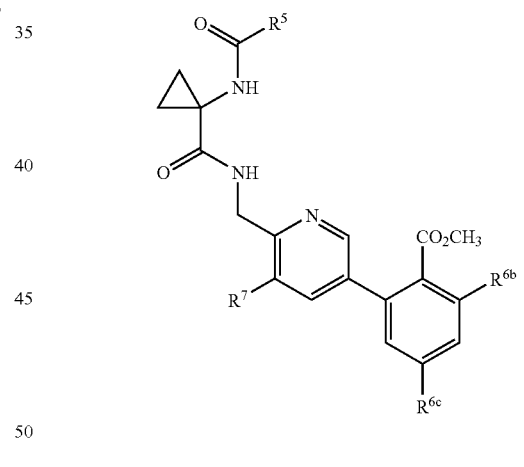

| Example | R$^5$ | R$^{6b}$ | R$^{6c}$ | R$^7$ | M + H$^+$ |
|---|---|---|---|---|---|
| 21 | dichlorofluorophenyl | Cl | H | F | 490 |
| 22 | difluoromethyl | Cl | H | F | 454 |
| 23 | NH(CO$_2$Me) | Cl | H | Cl | 493 |
| 24 | NH(CO$_2$Me) | Cl | H | H | 458 |
| 25 | trifluoromethyl | H | Cl | Cl | 490 |
| 26 | trifluoromethyl | Cl | Cl | Cl | 524 |
| 27 | trifluoromethyl | Cl | Cl | F | 508 |
| 28 | trifluoromethyl | F | Cl | Cl | 508 |
| 29 | trifluoromethyl | F | Cli | F | 492 |

The following compounds in Tables 3, 4 and 5 were prepared by methods us to those described in Example 2 and Example 3.

TABLE 3

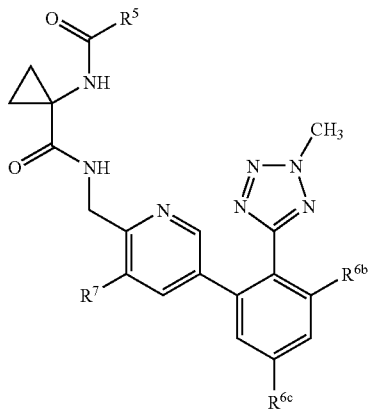

| Example | R5 | R6b | R6c | R7 | ES MS, M + H+ |
|---|---|---|---|---|---|
| 30 | pyrimidin-5-yl | F | H | Cl | 545 |
| 31 | chlorodifluoromethyl | F | H | Cl | 515 |
| 32 | trifluoromethyl | F | H | F | 482 |
| 33 | difluoromethyl | F | H | Cl | 480 |
| 34 | difluoromethyl | F | H | F | 464 |
| 35 | CF$_2$Cl | F | H | F | 496 |
| 36 | CF$_3$ | Cl | H | Cl | 514 |
| 37 | CF$_2$H | Cl | H | Cl | 496 |
| 38 | CH$_3$ | Cl | H | Cl | 460 |
| 39 | NHCO$_2$Me | Cl | H | Cl | 519 |
| 40 | CF$_3$ | H | Cl | Cl | 514 |
| 41 | CF$_3$ | Cl | Cl | F | 532 |
| 42 | CF$_3$ | Cl | Cl | Cl | 548 |
| 43 | CF$_3$ | F | Cl | Cl | 532 |
| 44 | CF$_3$ | F | Cl | F | 516 |

TABLE 4

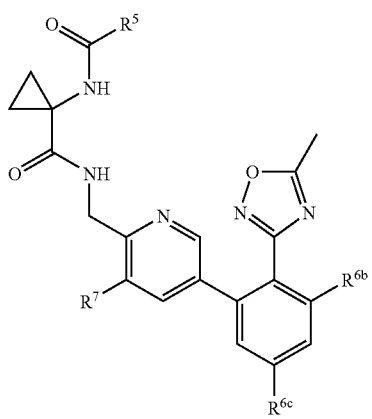

| Example | R5 | R6b | R6c | R7 | M + H+ |
|---|---|---|---|---|---|
| 45 | CF$_3$ | H | Cl | Cl | 514 |
| 46 | CF$_3$ | Cl | Cl | Cl | 547 |
| 47 | CF$_3$ | Cl | Cl | F | 532 |

TABLE 5

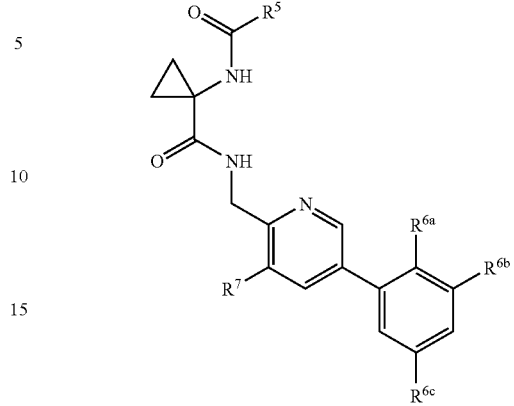

| Example | R5 | R6a | R6b | R6c | R7 | M + H+ |
|---|---|---|---|---|---|---|
| 48 | CF$_3$ | OCH$_2$CHF$_2$ | H | Cl | Cl | 512 |
| 49 | CF$_3$ | OCH(CH$_2$F)$_2$ | Cl | Cl | Cl | 559 |
| 50 | CF$_3$ | OCH(CH$_2$F)$_2$ | Cl | Cl | H | 526 |
| 51 | CF$_3$ | OCO$_2$Me | F | H | F | 474 |

EXAMPLE 52

Methyl 2,4-dichloro-6-(5-fluoro-6-{(1R)-1-[({1-[(trifluoroacetyl)amino]cyclopropyl}-carbonyl)amino]ethyl}pyridin-3-yl)benzoate

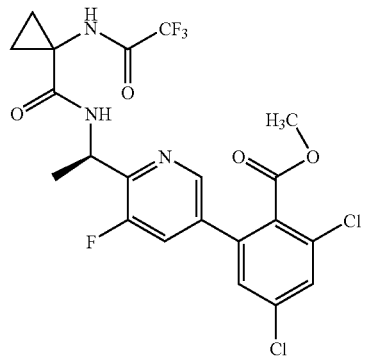

A solution of 2,4-dichloro-6-hydroxybenzaldehyde (5.00 g, 26.18 mmol) in 125 mL methanol was cooled to 0° C. Perchloric acid (70%, 1.47 mL, 16.23 mmol) was added, and the solution was stirred for 10 minutes. To a separate flask, vanadium (V) oxide (0.190 g, 1.05 mmol) was added to a hydrogen peroxide solution (30% in H$_2$O, 11.90 mL, 104.7 mmol) at 0° C. This solution was stirred until the catalyst was dissolved, resulting in a clear orange solution, which was added dropwise to the methanol solution. The reaction was allowed to slowly warm to room temperature and stir overnight. The solution was concentrated under vacuum, and the residue dissolved in ethyl acetate. The organic extract was washed with aqueous sodium bicarbonate and brine, dried over Na$_2$SO$_4$, filtered and concentrated. The residue was filtered through a silica gel plug with 10% ethyl acetate in hexanes to provide methyl 2,4-dichloro-6-hydroxybenzoate that gave proton NMR spectra consistent with theory.

A solution of 2,4-dichloro-6-hydroxybenzoate (4.64 g, 20.99 mmol) and pyridine (1.87 mL, 23.09 mmol) in 100 mL CH$_2$Cl$_2$ was cooled to 0° C. Trifluoromethanesulfonic acid (4.94 mL, 29.39 mmol) was added, and the solution was stirred for 2 h. The reaction mixture was washed with aqueous sodium bicarbonate, aqueous copper sulfate and brine, dried over Na$_2$SO$_4$, filtered and concentrated to provide methyl 2,4-dichloro-6-{[(trifluoromethyl)sulfonyl]oxy}-benzoate that gave proton NMR spectra consistent with theory.

To a solution of 5-bromo-3-nitropyridine-2-carbonitrile (4.71 g, 20.7 mmol) in MeOH (319 mL) under N$_2$ was added tin(II) chloride dihydrate (27.97 g, 123.9 mmol). The reaction was heated to 40° C. for 40 minutes, concentrated in vacuo, and azeotroped with toluene. The residue was dissolved in ethyl acetate, and 10% aqueous sodium bicarbonate was added till the solution was basic. The aqueous layer was extracted 3× with CHCl$_3$ and the combined organics were dried over Na$_2$SO$_4$, filtered and concentrated under vacuum to provide 3-amino-5-bromopyridine-2-carboxamide that gave a mass ion (ES+) of 218.2 for M+H$^+$($^{81}$Br).

To a solution of 3-amino-5-bromopyridine-2-carboxamide (40.0 g, 185.2 mmol) in CH$_2$Cl$_2$ was added nitrosonium tetrafluoroborate (22.71 g, 191.4 mmol). The reaction was stirred at room temperature for 4.5 hours, then concentrated in vacuo and azeotroped with toluene. The residue was suspended in toluene (1100 mL) and heated to 100° C. for 2 hours. The reaction was concentrated in vacuo, and the residue suspended in CH$_2$Cl$_2$. The solid was collected to provide 5-bromo-3-fluoropyridine-2-carboxamide that gave proton NMR spectra consistent with theory and a mass ion (ES+) of 219.1 for M+H$^+$($^{79}$Br).

A solution of crude 5-bromo-3-fluoropyridine-2-carboxamide (40.50 g, 184.9 mmol) in HCl (12N, 539.4 mL, 6.472 mol) was heated to 120° C. for 1 hour. The reaction was cooled to room temperature, and NaOH (20%) was added slowly to pH~6. The solution was concentrated in vacuo, and azeotroped 3×with toluene. The residue was extracted thoroughly with 40% MeOH/CHCl$_3$ and filtered. This was repeated three times. The combined filtrates were concentrated and azeotroped 3×with toluene to provide 5-bromo-3-fluoropyridine-2-carboxylic acid that gave a mass ion (ES+) of 218.1 for M+H$^+$($^{79}$Br).

A solution of crude 5-bromo-3-fluoropyridine-2-carboxylic acid (40.65 g, 184.8 mmol), O,N-dimethylhydroxylamine hydrochloride (21.63 g, 221.7 mmol), 1-ethyl-(3-dimethylaminopropyl)-carbodiimide hydrochloride (70.85 g, 369.6 mmol), 1-hydroxy-7-azabenzotriazole (2.497 g, 18.48 mmol), and triethylamine (16.48 mL, 118.3 mmol) in 200 mL DMF was stirred at room temperature overnight. The solution was partially concentrated in vacuo and partitioned between ethyl acetate and 10% aqueous sodium bicarbonate. The aqueous layer was extracted 4× with ethyl acetate, and the combined organics were washed with water and brine, dried over Na$_2$SO$_4$, filtered and concentrated under vacuum to provide 5-bromo-3-fluoro-N-methoxy-N-methylpyridine-2-carboxamide that gave proton NMR spectra consistent with theory and a mass ion (ES+) of 263.01 for M+H$^+$($^{79}$Br).

To a solution of crude 5-bromo-3-fluoro-N-methoxy-N-methylpyridine-2-carboxamide (27.94 g, 106.2 mmol) in THF (350 mL) at −78° C. was added lithium aluminum hydride (1M in THF, 45.67 mL, 45.67 mmol) dropwise. The reaction was stirred at −78° C. for 2 hours, then H$_2$O (100 mL) and brine (100 mL) were added. The mixture was warmed to RT and partially concentrated in vacuo, diluted with ethyl acetate and filtered through celite. The aqueous layer was extracted 4× with ethyl acetate. The combined organics were washed with brine, dried over Na$_2$SO$_4$, filtered and concentrated under vacuum. The residue was filtered through a silica gel plug with 10% ethyl acetate in hexanes to provide 5-bromo-3-fluoropyridine-2-carbaldehyde that gave proton NMR spectra consistent with theory.

To a solution of (R)-(+)-2-methyl-2-propanesulfinamide (9.898 g, 81.67 mmol) in CH$_2$Cl$_2$ (160 mL) was added 5-bromo-3-fluoropyridine-2-carbaldehyde (16.66 g, 81.67 mmol), pyridinium p-toluenesulfonate (1.026 g, 4.08 mmol), and magnesium sulfate (49.15 g, 408.3 mmol). The reaction was stirred at room temperature overnight, then filtered through celite and concentrated in vacuo. The residue was subjected to silica gel chromatography eluted with 0 to 10% ethyl acetate in hexanes to provide N-[(1E)-(5-bromo-3-fluoropyridin-2-yl)methylidene]-2-methylpropane-2-sulfinamide that gave proton NMR spectra consistent with theory and a mass ion (ES+) of 307.0 for M+H$^+$ ($^{81}$Br).

A solution of N-[(1E)-(5-bromo-3-fluoropyridin-2-yl)methylidene]-2-methyl-propane-2-sulfinamide (18.63 g, 60.65 mmol) in CH$_2$Cl$_2$ (375 mL) was cooled to −50° C. under N$_2$. Methylmagnesium chloride (3M in THF, 30.32 mL, 90.97 mmol) was added dropwise, the reaction was stirred for 1 h. Additional methylmagnesium chloride (5.0 mL, 15.0 mmol) was added after 30 minutes to drive the reaction to completion. Water (200 mL) and brine (200 mL) were added, and the reaction allowed to warm to room temperature. The aqueous layer was extracted 4× with CH$_2$Cl$_2$, and the combined organics were dried over Na$_2$SO$_4$, filtered and concentrated under vacuum. The residue was subjected to silica gel chromatography eluted with 10–40% ethyl acetate in hexanes to provide N-[(1R)-1-(5-bromo-3-fluoropyridin-2-yl)ethyl]-2-methylpropane-2-sulfinamide that gave proton NMR spectra consistent with theory and a mass ion (ES+) of 325.0 for M+H$^+$($^{81}$Br).

A mixture of N-[(1R)-1-(5-bromo-3-fluoropyridin-2-yl) ethyl]-2-methylpropane-2-sulfinamide (0.500 g, 1.55 mmol), bis(pinacolato)diboron (0.412 g, 1.62 mmol), potassium acetate (0.456 g, 4.64 mmol), and [1,1'-bis(diphenylphosphino)ferrocene]palladium(II) dichloride (0.030 g, 0.041 mmol) in 5 mL DMF was heated to 90° C. under N$_2$ for 4 hours. Additional bis(pinacolato)diboron (0.295 g, 1.16 mmol) and 3-chloroperoxybenzoic acid (861 mg, 4.99 mmol) and [1,1'-bis(diphenylphosphino)ferrocene]palladium(II) dichloride (0.030 g, 0.041 mmol) were added to drive the reaction to completion. The reaction mixture was cooled to room temperature, and methyl 2,4-dichloro-6-{[(trifluoromethyl)sulfonyl]oxy}benzoate (0.546 g, 1.55 mmol), sodium carbonate (2M, 2.32 mL, 4.64 mmol), and [1,1'-bis(diphenylphosphino)-ferrocene]palladium (II) dichloride (0.003 g, 0.041 mmol) were added. The reaction mixture was heated to 90° C. 1.5 hours, then cooled to room temperature and partitioned between ethyl acetate and water. The organic extract was washed with water and brine, dried over Na$_2$SO$_4$, filtered and concentrated under vacuum. The residue was subjected to silica gel chromatography eluted with 0–30% ethyl acetate in hexanes to provide methyl 2-(6-{(1R)-1-[(tert-butylsulfinyl)amino]-ethyl}-5-fluoropyridin-3-yl)-4,6-dichlorobenzoate that gave proton NMR spectra consistent with theory.

To a solution of the above product in methanol (1.2 mL) was added HCl/dioxane solution (4M, 1.2 mL, 4.6 mmol). The solution was stirred at room temperature 30 minutes, then concentrated in vacuo to provide (1R)-1-{5-[3,5-dichloro-2-(methoxycarbonyl)phenyl]-3-fluoropyridin-2-yl}ethanaminium chloride that gave a mass ion (ES+) of 343.01 for M+H$^+$.

A solution of (1R)-1-{5-[3,5-dichloro-2-(methoxycarbonyl)phenyl]-3-fluoro-pyridin-2-yl}ethanaminium chloride (0.277 g, 0.73 mmol), 1-[(trifluoroacetyl)amino]cyclo-propanecarboxylic acid (0.160 g, 0.812 mmol), 1-ethyl-(3-dimethylaminopropyl)-carbodiimide hydrochloride (0.311 g, 1.62 mmol), 1-hydroxy-7-azabenzotriazole (0.010 g, 0.15 mmol), and triethylamine (0.45 mL, 3.25 mmol) in 5 mL $CH_2Cl_2$ was stirred at room temperature for 3 days. The solution was washed with aqueous sodium bicarbonate and brine, dried over $Na_2SO_4$, filtered and concentrated. The residue was subjected to silica gel chromatography eluted with 10–30% ethyl acetate in hexanes to provide methyl 2,4dichloro-6-(5-fluoro-6-{(1R)-1-[({1-[(trifluoroacetyl)amino]cyclopropyl}carbonyl)amino]ethyl}pyridin-3-yl)benzoate that gave proton NMR spectra consistent with theory and a mass ion (ES+) of 522.05 for M+H$^+$.

Compounds listed in Table 6 were prepared by methods analogous to those described in Example 52

TABLE 6

| Example | $R^5$ | $R^{6a}$ | $R^{6b}$ | $R^{6c}$ | $R^7$ | M + H$^+$ |
|---|---|---|---|---|---|---|
| 53 | $CHF_2$ | 2-Methyl tetrazole | F | H | Cl | 492 |
| 54 | $CF_3$ | 2-Methyl tetrazole | F | H | Cl | 510 |
| 55 | $CF_3$ | $CO_2Me$ | Cl | H | Cl | 504 |
| 56 | $CF_3$ | 3-methyl-1,2,4-oxadiazole | F | H | Cl | 510 |
| 57 | $CF_3$ | $CF_3$ | F | H | Cl | 496 |
| 58 | $CF_3$ | $CF_3$ | F | H | H | 464 |
| 59 | $CF_3$ | $CO_2Me$ | Cl | H | H | 468 |
| 60 | $CF_3$ | 5-methyl-1,2,4-oxadiazole | H | Cl | Cl | 528 |
| 61 | $CF_3$ | $CF_3$ | F | H | F | 482 |
| 62 | $CF_3$ | $CO_2Me$ | Cl | H | F | 488 |
| 63 | $CHF_2$ | $CO_2Me$ | Cl | H | F | 470 |
| 64 | $CF_3$ | $CF_3$ | Cl | H | F | 496 |
| 65 | $CF_3$ | $CO_2Me$ | Cl | Cl | F | 522 |
| 66 | $CF_3$ | $OCHF_2$ | F | H | F | 480 |
| 67 | $CF_3$ | $CF_3$ | H | Cl | F | 496 |
| 68 | $CF_3$ | 5-methyl-1,2,4-oxadiazole | Cl | Cl | F | 546 |
| 69 | $CF_3$ | $OCH_2CF_3$ | F | H | F | 512 |
| 70 | $CF_3$ | Cl | H | Cl | F | 464 |
| 71 | $CF_3$ | $OCH(CH_2F)_2$ | F | H | F | 508 |
| 72 | $CF_3$ | $OCH(CH_2F)_2$ | F | H | H | 490 |
| 73 | $CF_3$ | $OCH_2CF_2H$ | F | H | F | 494 |
| 74 | $CF_3$ | 2-methyl tetrazole | Cl | Cl | F | 546 |
| 75 | $CF_3$ | 2-methyl tetrazole | H | Cl | F | 512 |
| 76 | $CF_3$ | $CO_2Et$ | Cl | H | F | 502 |
| 77 | $CF_3$ | 2-methyl tetrazole | F | Cl | F | 528 |
| 78 | $CF_3$ | $CO_2Me$ | F | Cl | F | 504 |
| 79 | $CF_3$ | $CO_2CH_2CH_2F$ | Cl | H | F | 520 |
| 80 | $CF_2Cl$ | $CO_2Me$ | Cl | Cl | F | 538 |
| 81 | $CHF_2$ | $CO_2Me$ | Cl | Cl | F | 504 |
| 82 | $CF_3$ | $CO_2Et$ | F | Cl | Cl | 536 |
| 83 | $CF_3$ | $CO_2Et$ | Cl | Cl | F | 536 |
| 84 | $CF_3$ | $CO_2CH_2CH_2F$ | F | Cl | F | 538 |
| 85 | $CF_3$ | $CO_2Me$ | F | Cl | Cl | 522 |
| 86 | $CF_3$ | $CO_2CH_2CH_2F$ | F | Cl | Cl | 554 |
| 87 | $CH_3$ | 2-methyl tetrazole | F | Cl | Cl | 546 |
| 88 | $CF_3$ | $CO_2Et$ | Cl | H | Cl | 518 |
| 89 | $CF_3$ | $CO_2Et$ | F | Cl | F | 518 |
| 90 | ![isothiazole] | $CO_2Me$ | Cl | Cl | F | 538 |
| 91 | $CF_3$ | $CO_2Et$ | F | H | F | 486 |

TABLE 6-continued

| Example | R⁵ | R⁶ᵃ | R⁶ᵇ | R⁶ᶜ | R⁷ | M + H⁺ |
|---|---|---|---|---|---|---|
| 92 | CF₃ | CN | Cl | Cl | F | 489 |
| 93 | CF₃ | OCH₂CH₃ | F | Cl | F | 490 |
| 94 | CF₃ | OCH₂CH₂F | F | Cl | F | 526 |
| 95 | 1,2,5-thiadiazolyl | CO₂Et | Cl | H | Cl | 516 |
| 96 | CF₃ | OCH₂CH₃ | F | Cl | Cl | 508 |
| 97 | isoxazol-5-yl | OCH₂CH₃ | F | Cl | Cl | 543 |
| 98 | 1,2,5-thiadiazolyl | OCH₂CH₃ | F | Cl | Cl | 560 |
| 99 | 1,2,5-thiadiazolyl | CN | F | Cl | Cl | 541 |
| 100 | CF₃ | OCH₂CF₃ | F | Cl | Cl | 562 |
| 101 | 1,2,5-thiadiazolyl | CO₂Me | F | Cl | Cl | 504 |
| 102 | isoxazol-5-yl | CN | F | Cl | Cl | 489 |
| 103 | isoxazol-5-yl | CO₂Me | F | Cl | H | 487 |
| 104 | isoxazol-5-yl | CO₂Me | F | Cl | Cl | 521 |
| 105 | CF₃ | CO₂CH₂CHF₂ | F | Cl | H | 538 |
| 106 | CF₃ | OCH₂CF₃ | F | Cl | Cl | 544 |

TABLE 6-continued

| Example | R⁵ | R⁶ᵃ | R⁶ᵇ | R⁶ᶜ | R⁷ | M + H⁺ |
|---|---|---|---|---|---|---|
| 107 | 1,2,5-thiadiazolyl | CO₂Et | F | Cl | Cl | 552 |
| 108 | CF₃ | OCH₂CF₂H | Cl | F | Cl | 544 |
| 109 | CF₃ | OCH₂CH₃ | Cl | F | Cl | 508 |
| 110 | 5-isoxazolyl | CO₂Et | F | Cl | Cl | 535 |
| 111 | 5-isoxazolyl | OCH₂CF₃ | F | Cl | Cl | 561 |
| 112 | 1,1-difluorocyclopropyl | OCH₂CF₃ | F | Cl | Cl | 570 |
| 113 | CF₃ | OCH₂CH₃ | F | F | Cl | 492 |
| 114 | CF₃ | OCH₂CF₂H | F | F | Cl | 528 |
| 115 | CF₃ | OCH₂CF₃ | Cl | F | Cl | 562 |
| 116 | 1,2,5-thiadiazolyl | CO₂Et | Cl | Cl | Cl | 534 |
| 117 | 5-isoxazolyl | OCH₂CF₂H | F | Cl | H | 543 |
| 118 | 5-isoxazolyl | CO₂Et | Cl | Cl | H | 517 |
| 119 | CF₃ | OCH₂CH₃ | Cl | Cl | Cl | 524 |
| 120 | CF₃ | OCH₂CF₂H | Cl | Cl | Cl | 560 |
| 121 | 5-isoxazolyl | OCH₂CF₂H | Cl | F | Cl | 543 |

TABLE 6-continued
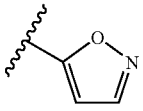
| Example | R⁵ | R⁶ᵃ | R⁶ᵇ | R⁶ᶜ | R⁷ | M + H⁺ |
|---|---|---|---|---|---|---|
| 122 | 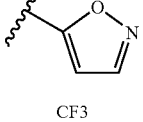 | OCH₂CH₃ | Cl | F | Cl | 507 |
| 123 | CF₃ | OCH₂CF₃ | Cl | Cl | Cl | 578 |
| 124 | CClF₂ | CO₂Et | F | Cl | H | 518 |
| 125 | CClF2 | CO₂Et | F | Cl | H | 518 |
| 126 |  | OCH₂CF₃ | Cl | F | Cl | 561 |
| 127 | CF3 | OCH₂CF₂H | F | Cl | Cl | 544 |
| 128 | 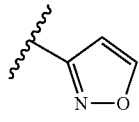 | OCH₂CF₃ | F | Cl | Cl | 570 |
| 129 | CF3 | OcPr | F | F | Cl | 502 |
| 130 | 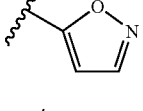 | OCH₂CF₂H | F | Cl | Cl | 543 |
| 131 | CF3 | CN | Cl | Cl | Cl | 542 |
| 132 | 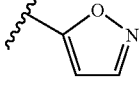 | OCH₂CH₃ | Cl | Cl | Cl | 522 |
| 133 | 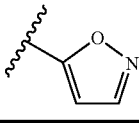 | OCH₂CF₂H | Cl | Cl | Cl | |
| 134 |  | OCH₂CF₃ | Cl | Cl | Cl | |

What is claimed is:

1. A compound of formula I and pharmaceutically acceptable salts thereof:

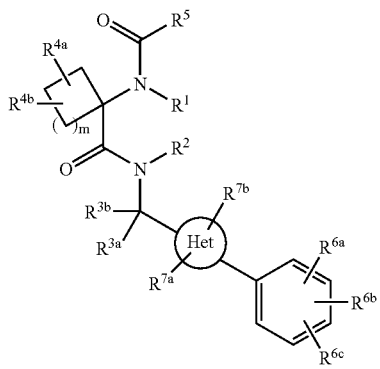

wherein

Het is pyrimidinyl or pyridyl, or N-oxide thereof;

$R^1$ and $R^2$ are independently selected from hydrogen and $C_{1-4}$ alkyl;

$R^{3a}$ and $R^{3b}$ are independently selected from hydrogen and $C_{1-4}$ alkyl optionally substituted with 1 to 5 halogen atoms;

$R^{4a}$ and $R^{4b}$ are independently selected form (1) hydrogen, (2) halogen, and (3) $C_{1-4}$ alkyl optionally substituted with 1 to 4 groups selected from halogen, $OR^a$, $OC(O)R^a$, $S(O)_kR^d$, $OS(O)_2R^d$, and $NR^1R^2$, or $R^{4a}$ and $R^{4b}$ together with the carbon atom to which they are both attached form an exo-cyclic methylene optionally substituted with 1 to 2 groups selected from $C_{1-4}$ alkyl optionally substituted with 1–5 halogen atoms and $C_{1-4}$ alkyloxy;

$R^5$ is selected from (1) $C_{1-6}$ alkyl optionally substituted with 1 to 5 groups independently selected from halogen, nitro, cyano, $OR^a$, $SR^a$, $COR^a$, $SO_2R^d$, $CO_2R^a$, $OC(O)R^a$, $NR^bR^c$, $NR^bC(O)R^a$, $NR^bC(O)_2R^a$, $C(O)NR^bR^c$, $C_{3-8}$ cycloalkyl, (2) $C_{3-8}$ cycloalkyl optionally substituted with 1 to 5 groups independently selected from halogen, nitro, cyano and phenyl, (3) $C_{3-6}$ alkynyl, (4) $C_{2-6}$ alkenyl optionally substituted with hydroxyethyl, (5) $(CH_2)_k$-aryl optionally substituted with 1 to 3 groups independently selected from halogen, nitro, cyano, $OR^a$, $SR^a$, $C(O)_2R^a$, $C_{1-4}$ alkyl and $C_{1-3}$ haloalkyl, wherein aryl is selected from phenyl, 3,4-methylenedioxyphenyl and naphthyl, (6) $(CH_2)_k$-heterocycle optionally substituted with 1 to 3 groups independently selected from halogen, nitro, cyano, $OR^a$, $SR^a$, $C_{1-4}$ alkyl and $C_{1-3}$ halo-alkyl wherein said heterocycle is selected from (a) a 5-membered heteroaromatic ring having a ring heteroatom selected from N, O and S, and optionally having up to 3 additional ring nitrogen atoms wherein said ring is optionally benzo-fused; (b) a 6-membered heteroaromatic ring containing from 1 to 3 ring nitrogen atoms and N-oxides thereof, wherein said ring is optionally benzo-fused; and (c) a 5- or 6-membered non-aromatic heterocyclic ring selected from tetrahydrofuranyl, 5-oxotetrahydrofuranyl, 2-oxo-2H-pyranyl, and 6-oxo-1,6-dihydropyridazinyl, (7) $C(O)_2R^a$, (8) $C(O)NR^bR^c$, and (9) $NR^bCO_2R^a$;

$R^{6a}$ is selected from (1) $C_{1-8}$ alkyl optionally substituted with 1–5 groups independently selected from halogen, nitro, cyano, $COR^a$, $CO_2R^a$, $C(O)NR^bR^c$, $OR^a$, $OC(O)R^a$, $SR^a$, $SO_2R^d$, $S(O)R^d$, $NR^bR^c$, $NR^bC(O)R^a$, $NR^bSO_2R^d$, $NR^bCO_2R^a$, (2) $C_{3-8}$ cycloalkyl, (3) $C_{2-8}$ alkenyl optionally substituted with $CO_2R^a$, (4) halogen, (5) cyano, (6) nitro, (7) $NR^bR^c$, (8) $NR^bC(O)R^a$, (9) $NR^bCO_2R^a$, (10) $NR^bC(O)NR^bR^c$, (11) $NR^bC(O)NR^bCO_2R^a$, (12) $NR^bSO_2R^d$, (13) $CO_2R^a$, (14) $COR^a$, (15) $C(O)NR^bR^c$, (16) $C(O)NHOR^a$, (17) $C(=NOR^a)R^a$, (18) $C(=NOR^a)NR^bR^c$, (19) $OR^a$, (20) $OC(O)_kR^a$, (21) $S(O)_kR^d$, (22) $SO_2NR^bR^c$, and (23) optionally substituted heterocycle where the heterocycle is selected from (a) a 5-membered heteroaromatic ring having a ring heteroatom selected from N, O and S, and optionally having up to 3 additional ring nitrogen atoms, (b) 4,5-dihydro-oxazolyl, and (3) 4,5-dihydro-1,2,4-oxadiazolyl, and wherein said substituent is 1 to 3 groups independently selected from $C_{1-4}$ alkyl optionally substituted with 1 to 5 halogen atoms, $OR^a$ or $OC(O)R^a$, $R^{6b}$ and $R^{6c}$ are independently selected from hydrogen, and a group from $R^{6a}$; with the proviso that not more than one of $R^{6a}$, $R^{6b}$, and $R^{6c}$ is a heterocycle;

$R^{7a}$ and $R^{7b}$ are independently selected from hydrogen, halogen, cyano, nitro, $OR^a$, $CO_2R^a$, $C(O)NR^bR^c$, $SO_2R^d$, $NR^bR^c$, and $C_{1-4}$ alkyl optionally substituted with 1 to 5 halogen atoms;

$R^a$ is selected from (1) hydrogen, (2) $C_{1-4}$ alkyl optionally substituted with 1 to 5 halogen atoms, (3) phenyl optionally substituted with 1 to 3 groups independently selected from halogen, cyano, nitro, OH, $C_{1-4}$ alkyloxy, $C_{3-6}$ cycloalkyl and $C_{1-4}$ alkyl optionally substituted with 1 to 5 halogen atoms, (4) $C_{3-6}$ cycloalkyl, and (5) pyridyl;

$R^b$ and $R^c$ are independently selected from (1) hydrogen, (2) $C_{1-4}$ alkyl optionally substituted with 1 to 5 groups independently selected from halogen, amino, mono-$C_{1-4}$alkylamino, di-$C_{1-4}$alkylamino, and $SO_2R^d$, (3) $(CH_2)k$-phenyl optionally substituted with 1 to 3 groups selected from halogen, cyano, nitro, OH, $C_{1-4}$ alkyloxy, $C_{3-6}$ cycloalkyl and $C_{1-4}$ alkyl optionally substituted with 1 to 5 halogen atoms, and (4) $C_{3-6}$ cycloalkyl, or $R^b$ and $R^c$ together with the nitrogen atom to which they are attached form a 4-, 5-, or 6-membered ring optionally containing an additional heteroatom selected from N, O, and S; or $R^b$ and $R^c$ together with the nitrogen atom to which they are attached form a cyclic imide;

$R^d$ is selected from (1) $C_{1-4}$ alkyl optionally substituted with 1 to 5 halogen atoms, (2) $C_{1-4}$ alkyloxy, and (3) phenyl optionally substituted with 1 to 3 groups selected from halogen, cyano, nitro, OH, $C_{1-4}$ alkyloxy, $C_{3-6}$ cycloalkyl and $C_{1-4}$ alkyl optionally substituted with 1 to 5 halogen atoms;

k is 0, 1 or 2; and m is 0, 1, 2 or 3.

2. A compound of claim 1 wherein $R^5$ is (1) $C_{1-6}$ alkyl optionally substituted with 1 to 5 groups independently selected from halogen, nitro, cyano, $OR^a$, $SR^a$, $COR^a$, $SO_2R^d$, $CO_2R^a$, $OC(O)R^a$, $NR^bR^c$, $NR^bC(O)R^a$, $C(O)NR^bR^c$, and $C_{3-8}$ cycloalkyl, (2) 1,2,5-thiadiazolyl, (3) isoxazolyl, (4) isothiazolyl or (5) pyrimidinyl.

3. A compound of claim 1 wherein $R^5$ is $C_{1-3}$ alkyl optionally substituted with 1 to 5 halogen atoms wherein said halogen is chloro or fluoro.

4. A compound of claim 1 wherein $R^5$ is selected from difluoromethyl, dichloromethyl, chlorodifluoromethyl, trifluoromethyl, 1,1-dichloroethyl and 2,2,2-trifluoroethyl.

5. A compound of claim 1 wherein $R^5$ is pyrimidinyl.

6. A compound of claim 1 wherein $R^5$ is 1,2,5-thiadiazolyl, isoxazolyl or isothiazolyl.

7. A compound of claim 1 wherein $R^{6a}$ is $OR^a$, $CO_2R^a$ or tetrazolyl optionally substituted with $C_{1-4}$ alkyl.

8. A compound of claim 1 wherein $R^{6a}$ is $OR^a$, $CO_2R^a$ or tetrazolyl optionally substituted with $C_{1-4}$ alkyl, $R^{6b}$ is hydrogen or halogen, and $R^{6c}$ is hydrogen or halogen.

9. A compound of claim 1 wherein $R^{6a}$ is methoxycarbonyl, ethoxycarbonyl, $C_{1-4}$alkoxy optionally substituted with 1 to 5 halogen atoms, or 2-methyl-2H-tetrazol-5-yl, $R^{6b}$ is fluoro or chloro, and $R^{6c}$ is hydrogen, chloro or fluoro.

10. A compound of claim 1 wherein Het is 2,5-pyridinediyl and $R^{7a}$ and $R^{7b}$ are independently hydrogen or halogen.

11. A compound of claim 10 wherein one of $R^{7a}$ and $R^{7b}$ is hydrogen and the other is fluoro or chloro.

12. A compound of claim 1 wherein m is 0 or 1.

13. A compound of claim 1 having formula Ia:

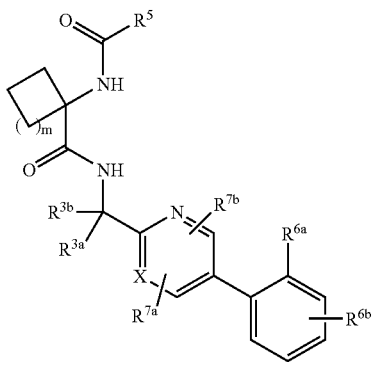

wherein X is carbon or nitrogen, and all other variables are as defined claim 1.

14. A compound of claim 13 wherein m is 0 or 1 and one of $R^{3a}$ and $R^{3b}$ is hydrogen and the other is hydrogen or $C_{1-3}$alkyl.

15. A compound of claim 13 wherein X is carbon, $R^{7a}$ is hydrogen or chloro or fluoro, and $R^{7b}$ is hydrogen.

16. A compound of claim 13 wherein X is nitrogen and $R^{7a}$ and $R^{7b}$ are each hydrogen.

17. A compound of claim 1 having formula Ib:

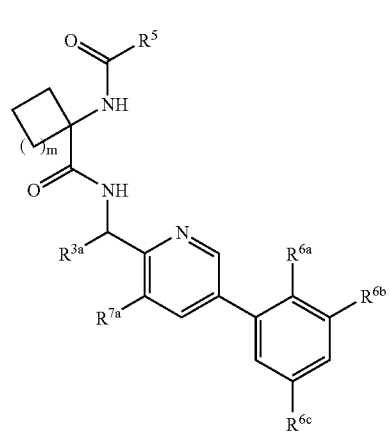

wherein m is 0 or 1, $R^{3a}$ is hydrogen or methyl, $R^{6b}$ and $R^{6c}$ are independently hydrogen, chloro or fluoro, $R^{7a}$ is hydrogen, chloro or fluoro, and the other variables are as defined in claim 1.

18. A compound of claim 17 wherein $R^{3a}$ is hydrogen, and $R^{6b}$ and $R^{7a}$ are each indepedently chloro or fluoro.

19. A compound of claim 17 wherein $R^{3a}$ is hydrogen, $R^{6b}$ and $R^{7a}$ are each indepedently chloro or fluoro, $R^5$ is selected from isoxazolyl, thiazolyl, 1,2,5-thiadiazolyl, 5-pyrimidinyl and $C_{1-2}$alkyl substituted with 1 to 3 halogen atoms selected from chloro and fluoro, and $R^{6a}$ is $OR^a$, $CO_2R^a$ or 2-methyl-5-tetrazolyl.

20. A compound of claim 1 having the formula Ic:

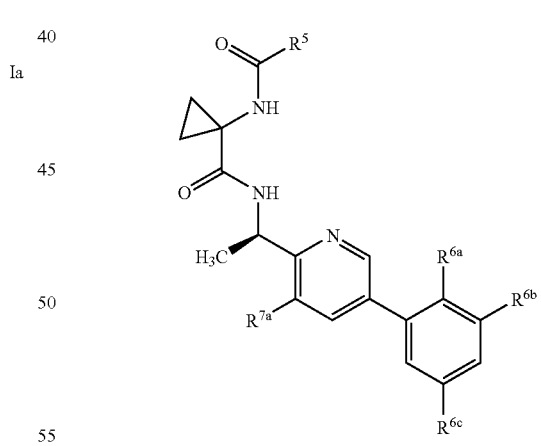

wherein $R^5$, $R^{6a}$, $R^{6b}$, $R^{6c}$ and $R^{7a}$ are as defined in claim 1.

21. A compound of claim 20 wherein $R^{6b}$ is halogen, and $R^{6c}$ and $R^{7a}$ are independently hydrogen or halogen.

22. A compound of claim 20 wherein $R^5$ is selected from isoxazolyl, isothiazolyl, 1,2,5-thiadiazolyl, 5-pyriridinyl and $C_{1-2}$alkyl substituted with 1 to 5 halogen atoms.

23. A compound of claim 21 wherein $R^5$ is selected from isoxazolyl, isothiazolyl, 1,2,5-thiadiazolyl, 5-pyrimidinyl and $C_{1-2}$alkyl substituted with 1 to 5 halogen atoms.

24. A compound of claim 20 wherein $R^{6a}$ is selected from $CO_2C_{1-4}$alkyl, $C_{1-4}$alkoxy optionally substituted with 1 to 5 halogen atoms and 2-methyl-5-tetrazolyl.

25. A compound of claim 23 wherein $R^{6a}$ is selected from $CO_2C_{1-4}$alkyl, $C_{1-4}$alkoxy optionally substituted with 1 to 5 halogen atoms and 2-methyl-5-tetrazolyl.

26. A pharmaceutical composition comprising a therapeutically effective amount of a compound of claim 1 and pharmaceutically acceptable excipients.

* * * * *